US010120975B2

(12) United States Patent
Fusi et al.

(10) Patent No.: US 10,120,975 B2
(45) Date of Patent: Nov. 6, 2018

(54) COMPUTATIONALLY EFFICIENT CORRELATION OF GENETIC EFFECTS WITH FUNCTION-VALUED TRAITS

(71) Applicant: Microsoft Technology Licensing, LLC, Redmond, WA (US)

(72) Inventors: Nicolo Fusi, Boston, MA (US); Jennifer Listgarten, Cambridge, MA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 381 days.

(21) Appl. No.: 15/084,951

(22) Filed: Mar. 30, 2016

(65) Prior Publication Data

US 2017/0286593 A1   Oct. 5, 2017

(51) Int. Cl.
| | | |
|---|---|---|
| *G01N 33/48* | (2006.01) | |
| *G01N 33/50* | (2006.01) | |
| *G06F 19/18* | (2011.01) | |
| *G06F 19/24* | (2011.01) | |

(52) U.S. Cl.
CPC .............. *G06F 19/18* (2013.01); *G06F 19/24* (2013.01)

(58) Field of Classification Search
None
See application file for complete search history.

(56) References Cited

U.S. PATENT DOCUMENTS

| 8,046,200 B2 | 10/2011 | Kirby et al. |
| 2005/0086035 A1 | 4/2005 | Peccoud et al. |
| 2010/0074864 A1 | 3/2010 | Achiron et al. |
| 2013/0064901 A1 | 3/2013 | Tan et al. |
| 2013/0296182 A1 | 11/2013 | Feinberg et al. |

FOREIGN PATENT DOCUMENTS

| WO | WO2012158897 A1 | 11/2012 |
| WO | WO2015042496 A1 | 3/2015 |

OTHER PUBLICATIONS

Burger, "Constraints for the Evolution of Functionally Coupled Characters: A Nonlinear Analysis of a Phenotypic Model", Evolution, 1986, vol. 40 (1), pp. 182-193.

(Continued)

*Primary Examiner* — Russell S Negin
(74) *Attorney, Agent, or Firm* — Drinker Biddle & Reath LLP

(57) ABSTRACT

This disclosure presents a model for identifying correlations in genome-wide association studies (GWAS) with function-valued traits that provides increased power and computational efficiency by use of a Gaussian process regression with radial basis function (RBF) kernels to model the function-valued traits and specialized factorizations to achieve speed. A Gaussian Process is assigned to each partition for each allele of a given single nucleotide polymorphism (SNP) which yields flexible alternative models and handles a large number of data points in a way that is statistically and computationally efficient. This model provides techniques for handling missing and unaligned function values such as would occur when not all individuals are measured at the same time points. If the data is complete algebraic re-factorization by decomposition into Kronecker products reduces the time complexity of this model thereby increasing processing speed and reducing memory usage as compared to a naive implementation.

20 Claims, 10 Drawing Sheets

(56) References Cited

OTHER PUBLICATIONS

Chung, et al., "Mixed-Effects Models for GAW18 Longitudinal Blood Pressure Data", BMC Proc., 2014, vol. 8 (Suppl 1); S87, 5 pages.
Das, et al., "A Dynamic Model for Genome-Wide Association Studies", Hum. Genet., 2011, vol. 129 (6), pp. 629-639.
Ding, et al., "Modeling of Multivariate Longitudinal Phenotypes in Family Genetic Studies with Bayesian Multiplicity Adjustment", BMC Proc., 2014, vol. 17 (8) (Suppl 1), S69, 6 pages.
Furlotte, et al., "Genome-Wide Association Mapping with Longitudinal Data", Genet Epidemiol., 2012, vol. 36 (5), pp. 463-471.
Fusi, et al., "Warped Linear Mixed Models for the Genetic Analysis of Transformed Phenotypes", Nat. Commun., 2014, 5:4890. 8 pgs.
Gonzalez, et al., "SNPassoc: An R Package to Perform Whole Genome Association Studies", Bioinformatics, 2007, vol. 23 (5), pp. 644-645.
Harchaoui, et al., "Kernal-Based Methods for Hypothesis Testing", IEEE Signal Processing Magazine, 2013, pp. 87-97.
He, et al., "Set-Based Tests for Genetic Association in Longitudinal Studies", Biometrics, vol. 71 (3), pp. 606-615.
Huang, et al., "Bayesian Association of Haplotypes and Non-Genetic Factors to Regulatory and Phenotypic Variation in Human Populations", Bioinformatics, 2007, vol. 23 (13), pp. i212-i221.
Jaffa, et al., "Analysis of Multivariate Longitudinal Kidney Function Outcomes Using Generalized Linear Mixed Models", J. Transl. Med., 2015, vol. 13 (192), 12 pages.
Kang, et al., "Efficient Control of Population Structure in Model Organism Association Mapping", Genetics, 2008, vol. 178 (3), 25 pages.
Kendziorski, et al., "Mapping Baroreceptor Function to Genome: A Mathematical Modeling Approach", Genetics, 2002, vol. 160 (4), pp. 1687-1695.
Lippert, et al., "FaST Linear Mixed Models for Genome-Wide Association Studies", Nat. Methods, 2011, vol. 8 (10), pp. 833-835.
Listgarten, et al., "A Powerful and Efficient Set Test for Genetic Markers that Handles Confounders", Bioinformatics, 2013, vol. 29 (12), pp. 1526-1533.
Listgarten, et al., "Correction for Hidden Confounders in the Genetic Analysis of Gene Expression", Proc. Natl. Acad. Sci., 2010, vol. 107 (38), pp. 16465-16470.
Liu, et al., "A Novel Adaptive Method for the Analysis of Next-Generation Sequencing Data to Detect Complex Trait Associations with Rare Variants Due to Gene Main Effects and Interactions", PLoS Genetics, 2010, vol. 6 (10), e1001156, 14 pages.
Musolf, et al., "Mapping Genes with Longitudinal Phenotypes via Bayesian Posterior Probabilities", BMC Proc., 2014, vol. 17 (8) (Suppl 1), S81, 5 pages.
Price, et al., "Principal Components Analysis Corrects for Stratification in Genome-Wide Association Studies", Nat. Genet., 2006, vol. 38 (8), pp. 904-909.
Quinonero-Candela, et al., "A Unifying View of Sparse Approximate Gaussian Process Regression", Journal of Machines Learning Research, 2005, vol. 6, pp. 1939-1959.
Rasmussen, et al., "Gaussian Processes for Machine Learning", The MIT Press, 2006, http://www.gaussianprocess.org/gpml/, 266 pages.
Shim, et al., "Wavelet-Based Genetic Association Analysis of Functional Phenotypes Arising from High-Throughput Sequencing Assays", The Annals of Applied Statistics, vol. 9 (2), 26 pages.
Sikorska, "Computationally Fast Approached to Genome-Wide Association Studies", Doctoral Dissertation, 2014, 131 pages.
Sikorska, et al., "GWAS with Longitudinal Phenotypes: Performance of Approximate Procedures", European Journal of Human Genet., vol. 23 (10), pp. 1384-1391.
Smith, et al., "Longitudinal Genome-Wide Association of Cardiovascular Disease Risk Factors in the Bogalusa Heart Study", PLoS Genet., 2010, vol. 6 (9), e1001094, 11 pages.
Stegle, et al., "Efficient Inference in Matrix-Variate Gaussian Models with iid Observation Noise", Advances in Neural Information Processing Systems 24, 2011, pp. 630-638.
Titsias, "Variational Learning of Inducing Variables in Sparse Gaussian Processes", Proceedings of the Twelfth International Conference on Artificial Intelligence and Statistics, 2009, pp. 567-574.
Wang, "Linear Mixed Effects Model for a Longitudinal Genome Wide Association Study of Lipid Measures in Type 1 Diabetes", McMaster University, 2012, 89 pages.
Wu, et al., "Powerful SNP-Set Analysis for Case-Control Genome-wide Association Studies", Am J. Jum Genet., 2010, vol. 86 (6), pp. 929-942.
Yu, et al., "A Unified Mixed-Model Method for Association Mapping that Accounts for Multiple Levels of Relatedness", Nat. Genet., 2006, vol. 38 (2), pp. 203-208.
Zhang, "Multivariate Adaptive Splines for Analysis of Longitudinal Data", Journal of Computational and Graphical Statistics, 1997, vol. 6 (1), pp. 74-91.

COMPUTATIONALLY EFFICIENT CORRELATION OF GENETIC EFFECTS WITH FUNCTION-VALUED TRAITS

BACKGROUND

Genome-wide association studies (GWAS) are a relatively new way to identify genes involved in an organism's traits. This method searches the genome for small variations, called single nucleotide polymorphisms (SNPs) that occur more frequently in organisms with a particular trait than in organisms without the trait. One use of GWAS is to identify SNPs associated with human traits. Each study can look at hundreds, thousands, or millions of SNPs at the same time. Data from GWAS show correlations between genetic variations and traits that are used to pinpoint genes that may contribute to developing the trait. Further research can identify if and how the genes may influence the trait.

Because genome-wide association studies examine SNPs across the genome, they represent a promising way to study traits in which many genetic variations contribute to the characteristics of an organism related to that trait. This approach has already identified SNPs related to several complex conditions including diabetes, heart abnormalities, Parkinson disease, and Crohn disease. Future genome-wide association studies may identify SNPs associated with other chronic diseases, as well as variations that affect a subject's response to certain drugs and influence interactions between a subject's genes and the environment.

GWAS commonly examine one trait at a time. Occasionally they examine several related traits with the hopes of increasing power; in such a setting, the traits are not generally smoothly varying in any way such as time or space. However, with the advent of wearables for health and the "quantified self" movement; the broad deployment of cheap sensors and the approaching ubiquity of electronic health records, abundant data from ubiquity of function-valued traits will be available for analysis by GWAS. Longitudinal traits are one example of function-valued traits—traits which can be viewed as a smooth function of some variable. For example, that variable could be time in a clinical history corresponding to a longitudinal trait, or it could be position in the genome corresponding to a spatial trait such as chromatin accessibility.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

This disclosure provides a new method for performing GWAS on function-valued traits based on Gaussian Process (GP) regression with a non-linear kernel at its core. This method identifies correlations between SNPs and traits of a subject. The methods of this disclosure are flexible in their capacity to handle a wide range of functional forms. This flexibility is achieved by using a non-parametric statistical model based on GP regression. Computations in this model are efficient when time points are aligned and traits are not missing, scaling only cubically with the number of time points as opposed to cubic in the number of time points times individuals, as would be the case in a naive computation. This efficiency is obtained in part by use of Kronecker products. Models discussed herein can also be adapted for efficient computations even in the presence of missing trait data or unaligned samples by use of pseudo-inputs and pseudo-parameters to perform variational inference.

DESCRIPTION OF THE DRAWINGS

The Detailed Description references the accompanying figures. In the figures, the left-most digit(s) of a reference number identifies the figure in which the reference number first appears. The use of the same reference numbers in different figures indicates similar or identical items.

DETAILED DESCRIPTION

Figure 1:
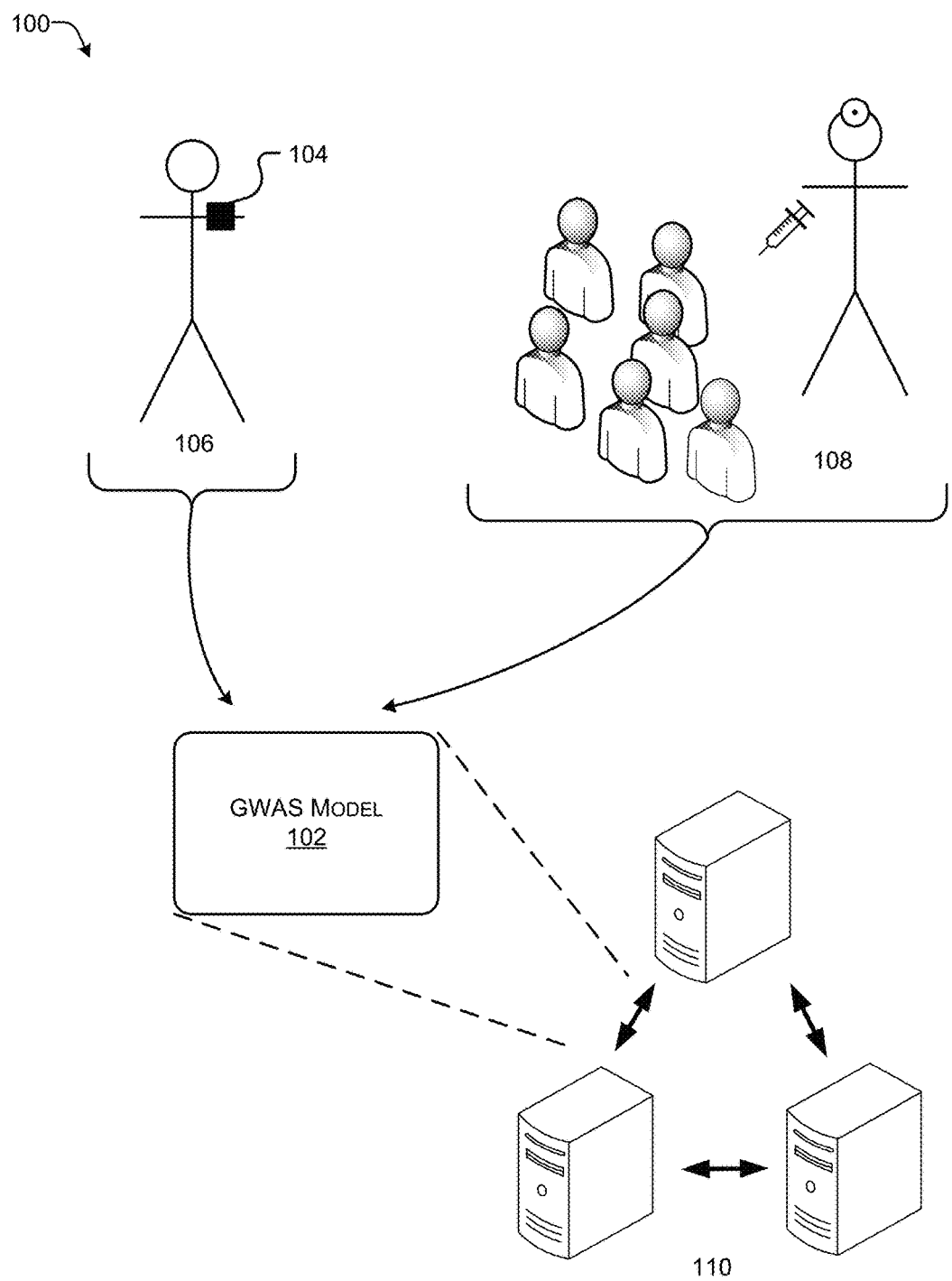
FIG. 1 shows an illustrative architecture for using a GWAS model to identify correlations between SNPs and traits.

Analysis of function-valued traits can potentially provide new insights into genetics. However, function-valued traits provide data for a trait across time (or other variable) leading to a much larger volume of data to analyze that for a trait that only has a single value. Benefiting from potential insights provided by analysis of function-valued traits while handling the increased volume of data is accomplished by recognizing that the rich, smoothly-varying structure within these traits can be leveraged by selecting and modifying an appropriate statistical model. Examples of rich trait structure are constraints in the physical world such as that: time moves forward and is smoothly varying, the correlation between positions on the genome is slowly decreasing according to genetic distance on the chromosome, or the size of a feature in a magnetic-resonance image (MRI) will change only gradually from one image slice to the next. Modelling approaches in these settings should take into account such constraints while still allowing for flexibility in the "shapes" of the traits. Accounting for "shape" or traits recognizes that a given genetic effect might alter the functional form of a function-valued trait, such as the shape of a growth curve, a pattern of weight gain, bone loss, or electrocardiogram signal in a more complex way than simply increasing or decreasing all values by the same amount. GWAS can identify which if any SNPs correlate with the shape of the trait. The correlation may be a linear or a non-linear correlation. Thus, this disclosure provides techniques for flexible modelling that can account for effects more complex than linear genetic effects.

The model presented in this disclosure uses Gaussian process (GP) regression. Modifications to basic GP regression described herein include the use of Kronecker-product-based refactorizations of matrix-variate normal probability distributions. Examples of non-linear kernels include Radial Basis Function (RBF) kernels and Matern kernels. Kronecker-product-based refactorizations yield computational efficiencies in the case of aligned and non-missing function domain points. Use of variational approximations further reduces computational time complexity when there are missing data or unaligned function domain points.

Single nucleotide polymorphisms, frequently called SNPs (pronounced "snips"), are a common type of genetic variation. Each SNP represents a difference in a single DNA building block, called a nucleotide. For example, a SNP may replace the nucleotide cytosine (C) with the nucleotide thymine (T) in a certain stretch of DNA.

SNPs occur normally throughout a subject's DNA. They occur once in every 300 nucleotides on average, which means there are roughly 10 million SNPs in the human genome. Most commonly, these variations are found in the DNA between genes. They can act as biological markers, helping scientists locate genes that are associated with disease. When SNPs occur within a gene or in a regulatory region near a gene, they may play a more direct role in disease by affecting the gene's function.

Most SNPs have no effect on health or development. Some of these genetic differences, however, have proven to be very important in the study of human health. Researchers have found SNPs that may help predict an individual's response to certain drugs, susceptibility to environmental factors such as toxins, and risk of developing particular diseases. SNPs can also be used to track the inheritance of disease genes within families.

A GWAS is an examination of many typically common genetic variants in different individual subjects to see if any variant is associated with a trait. GWAS typically focus on associations between SNPs and traits like major diseases. GWAS compare the DNA of subjects having varying phenotypes for a particular trait or disease. Participants in a GWAS study may be people with a disease (cases) and similar people without (controls), or they may be people with different phenotypes for a particular trait, for example blood pressure. This approach is known as phenotype-first, in which the participants are classified first by their clinical manifestation(s), as opposed to genotype-first. Each subject gives a sample of DNA, from which millions of genetic variants are read using SNP arrays. There are small variations in the individual nucleotides of the genomes (SNPs) as well as many larger variations, such as deletions, insertions and copy number variations. Any of these may cause alterations in an individual's traits, or phenotype, which can be anything from disease risk to physical properties such as height. If one type of the variant (one allele) is more frequent in subjects with the disease, the variant is said to be associated with the disease. The associated SNPs are then considered to mark a region of the genome that may influence the risk of disease. In contrast to methods that specifically test one or a few genetic regions, the GWAS investigate the entire genome. The approach is therefore said to be non-candidate-driven in contrast to gene-specific candidate-driven studies. GWAS identify SNPs and other variants in DNA associated with a disease, but cannot on their own specify which genes are causal.

An allele is one of a number of alternative forms of the same gene or same genetic locus. Sometimes, different alleles can result in different observable phenotypic traits, such as different pigmentation. However, most genetic variations result in little or no observable variation. Most multicellular organisms have two sets of chromosomes; that is, they are diploid. These chromosomes are referred to as homologous chromosomes. If both alleles are the same, they and the organism are homozygous with respect to that gene. If the alleles are different, they and the organism are heterozygous with respect to that gene. Thus, for most organisms there will be three allele possibilities: homozygous wild-type, heterozygous, and homozygous mutant.

Searching for a correlation between an individual SNP and a trait of interest, a so-called marginal test, is simpler than examining interactions between multiple SNPs. A SNP that determined to be correlated with the trait is then assumed to have a reasonable probability of being causal for the trait, or of tagging a nearby SNP that is causal for the trait. One solution to this marginal testing problem entails (1) proposing a statistical model of the data, and (2) obtaining some weight-of-evidence of a genetic effect such as a p-value or Bayes factor.

Some existing approaches for analyzing function-valued genetic associations do not use of the rich trait structure to increase power because they these approaches often assume restrictive forms of the genetic effect or the trait itself. In addition, in some approaches, the statistical efficiency does not scale well with the number of function domain points, which will be numerous for frequently-sampled function-valued traits.

The statistical power or sensitivity of a binary hypothesis test is the probability that the test correctly rejects the null hypothesis when the alternative hypothesis is true. Statistical power (or just "power") may also be thought of as the probability of accepting the alternative hypothesis when it is true—that is, the ability of a test to detect an effect, if the effect actually exists. A type I error, also known as an error of the first kind, occurs when the null hypothesis ($H_0$) is true, but is rejected. It is asserting something that is absent, a false hit. A type I error may be compared with a so-called false positive (a result that indicates that a given condition is present when it actually is not present) in tests where a single condition is tested for. The type I error rate or significance level is the probability of rejecting the null hypothesis given that it is true.

Standard frequentist hypothesis testing uses a null model that is nested in the alternative model that then allows one to use a likelihood ratio or score test, for example. However, even when models are nested, these tests require that model assumptions are met, and typically that sample sizes are large enough for asymptotic to be valid.

FIG. 1 shows an illustrative architecture 100 for using a GWAS model 102 to identify correlations between SNPs and traits. Data to be analyzed by the GWAS model 102 may come from any source such as from a wearable device 104 on a person 106 (or animal), a device other than a wearable device such as a scale or MRI machine, or a clinical study 108. The wearable device 104 may collect readings of a trait of the person 106. The readings may be automatic and may be periodic (e.g., every 10 seconds, every minute, one-per day, etc.) or irregular. The wearable device 104 may also collect readings in response to an input provided by the person 106 who is wearing the wearable device 104 or by another individual. The wearable device 104 may be implemented as any type of device such as a wristband, heart-rate monitor, watch, headband, and the like. As used herein, wearable device 104 also includes implanted medical devices such as pacemakers, cochlear implants, etc. The wearable device 104 may measure any type of trait such as heart rate, blood pressure, temperature, brain activity, and the like. Frequent measurement of the trait may create a large number of data points (e.g. a reading every 10 seconds for a year creates 2,759,400 data points).

The GWAS model 102 may be implemented on a computing device(s) 110 that performs processing of data collected from the wearable device 104, clinical study 108, or other source. The computing device(s) 110 is illustrated in FIG. 1 as a computer cluster, but it may take any other configuration.

As mentioned above, the GWAS model 102 uses GP regression. GP regression have a fixed number of parameters that does not grow with the number of function domain points. This makes GP regression models suited for dealing with a large number of function domain points (e.g. time points). In a GP, every point in some input space is associated with a normally distributed random variable. Moreover, every finite collection of those random variables has a multivariate normal distribution. The distribution of a GP regression is the joint distribution of all those (infinitely many) random variables, and as such, it is a distribution over functions. GP regression can be seen as an infinite-dimensional generalization of multivariate normal distributions. A key fact of GP regressions is that they can be completely defined by their second-order statistics. Thus, if a GP regression is assumed to have mean zero, defining the covariance function completely defines the process' behavior. However, altering the implementation if the mean has a value other than zero is well within the skill of a person having ordinary skill in the art. The GWAS model 102 assumes that the functions representing the traits are smooth so measurements closer (e.g., in time or space) are more likely to be similar than measurements that are father apart. This is encoded by the kernel. The combination of a smoothly fitting function with a Gaussian distribution yields a GP.

The GWAS model 102 can capture any smoothly-varying trait (not only traits that vary in time), where the smoothness is controlled by a parameter. This parameter may be a length-scale parameter that is estimated using maximum likelihood, thereby effectively deducing the complexity of the trait functional form directly from the data. As for the genetic effect, there are three components corresponding to three partitions of the data, yielding an extremely non-restrictive class of genetic effects since the GP regression for a single allele can look completely different from the other alleles when no parameters are shared. However, the model need not be used in this manner. Furthermore, because the RBF kernel effectively integrates out the function domain point parameters, the number of model parameters does not scale with the number of function domain points, but is instead fixed—a beneficial property when many function domain points are observed.

Figure 2:
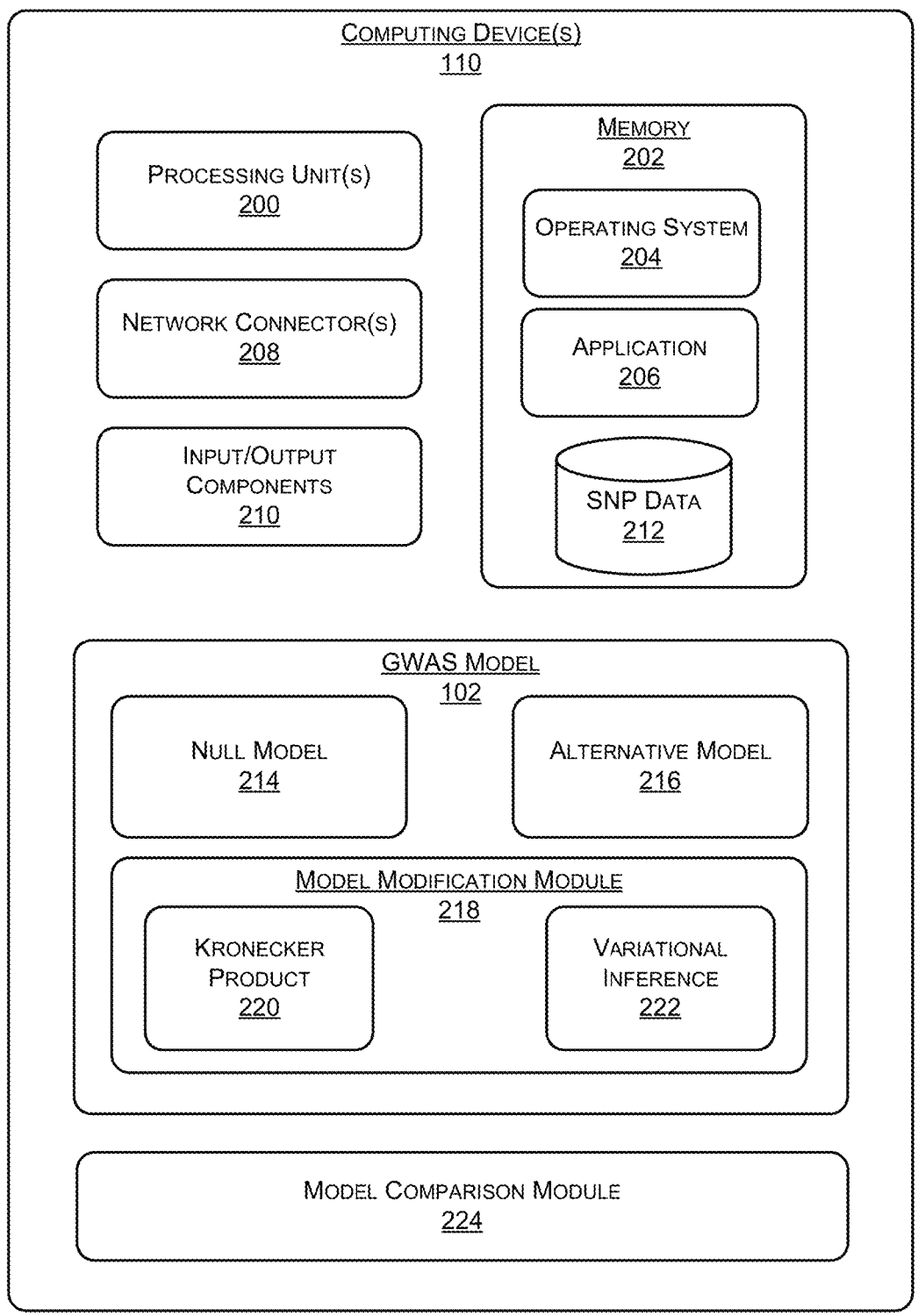
FIG. 2 shows an illustrative diagram of the computing device of FIG. 1.

FIG. 2 shows an illustrative diagram of the computing device(s) 110 first introduced in FIG. 1. The computing device(s) 110 may contain one or more processing unit(s) 200 and memory 202 both of which may be distributed across one or more physical or logical locations. The processing unit(s) 200 may include any combination of central processing units (CPUs), graphical processing units (GPUs), single core processors, multi-core processors, application-specific integrated circuits (ASICs), programmable circuits such as Field Programmable Gate Arrays (FPGA), and the like. One or more of the processing unit(s) 200 may be implemented in software and/or firmware in addition to hardware implementations. Software or firmware implementations of the processing unit(s) 200 may include computer- or machine-executable instructions written in any suitable programming language to perform the various functions described. Software implementations of the processing unit(s) 200 may be stored in whole or part in the memory 202. The memory 202 may also include an operating system (OS) 204 and one or more programs or applications 206 that are loadable and executable by processing unit(s) 200.

Alternatively, or in addition, the functionally of the computing devices 110 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Computing device(s) 110 may be connected to a network through one or more network connector(s) 208 for receiving and sending information. The network may be implemented as any type of communications network such as a local area network, a wide area network, a mesh network, and ad hoc network, a peer-to-peer network, the Internet, a cable network, a telephone network, and the like. In one implementation, the computing device(s) 110 may have a direct connection to one or more other devices (e.g. wearable device 104) without the presence of an intervening network. The direct connection may be implemented as a wired connection or a wireless connection. A wired connection may include one or more wires or cables physically connecting the computing device(s) 110 to another device. For example, the wired connection may be created by a headphone cable, a telephone cable, a SCSI cable, a USB cable, an Ethernet cable, or the like. The wireless connection may be created by radio frequency (e.g., any version of Bluetooth, ANT, Wi-Fi IEEE 802.11, etc.), infrared light, or the like.

The computing device(s) 110 may be a computer cluster, a supercomputer, a network server, a desktop computer, a notebook computer, a collection of server computers such as a server farm, a cloud computing system that uses processing power, memory, and other hardware resources distributed across multiple geographic locations, or the like. The computing device(s) 110 may include one or more input/output components(s) 210 such as a keyboard, a pointing device, a touchscreen, a microphone, a camera, a display, a speaker, a printer, and the like.

Memory 202 of the computing device(s) 110 may include removable storage, non-removable storage, local storage, and/or remote storage to provide storage of computer-readable instructions, data structures, program modules, and other data. The memory 202 may be implemented as computer-readable media. Computer-readable media includes, at least, two types of media, namely computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer readable instructions, data structures, program modules, or other data in a modulated data signal, such as a carrier wave, or other transmission mechanism. As defined herein, computer-readable storage media and communications media are mutually exclusive.

The computing device(s) 110 includes multiple modules that may be implemented as instructions stored in the memory 202 for execution by processing unit(s) 200 and/or implemented, in whole or in part, by one or more hardware logic components or firmware. The GWAS model 102 introduced in FIG. 1 is contained within the computing device(s) 110 and may be implemented as instructions stored in the memory 202 for execution by the processing unit(s) 200, by hardware logic components, or both.

The GWAS model 102 analyzes SNP data 212 that may be, but is not necessarily, stored in the memory 202. The SNP data 212 contains SNP genotype and indication of the phenotypic trait for a subject. For example, the SNP data 212 may identify a specific SNP, list the nucleotide present at that location in the genome, and identify the trait as either present or not present (e.g., for a disease state) or include a value for the trait (e.g, for height, blood pressure, etc.). The SNP data 212 may come from the wearable device 104, clinical study 108, or other source. Data from multiple sources may also be combined in the SNP data 212. Data for traits in the SNP data 212 may be stored as vectors. A series of measurements or readings across a function domain (e.g., time or space) for a trait of a subject (e.g., a human patient) can be represented as a vector. Vectors containing data from multiple subjects may be combined into a matrix.

The GWAS model 102 includes a null model 214. The null model 214 treats all subjects as having the same trait, other than noise, and includes assumptions that the trait is smoothly varying over the function domain and that all subjects respond to a genotype in the same way. The null model 214, $M_0$, assumes that the SNP has no effect on the trait (and so SNP is not included in the model). This represents the assumption that values of the trait are not correlated with the particular SNP being tested. However, the null model does capture correlation over the function domain because it uses a non-linear kernel. Let Y be the N×T matrix of traits for N subjects and T be function domain points. If there are missing or unaligned data, then the matrix is unrolled, in conjunction with the use of pseudo-inputs. Let W be the N×T points at which the traits were measured, and let vec(Y) denote the unrolled version of Y into a vector of dimension NT×1, $$vec(Y) = \begin{pmatrix} y_{11} \\ y_{21} \\ \vdots \\ y_{NT} \end{pmatrix}$$

then in Equation 1:

$$M_0: p(vec(Y)) = \mathcal{N}(vec(Y)|0, \sigma_r^2 K(W,W|l) + \sigma_e^2 I_{NT}) \quad (1)$$

where $\mathcal{N}(a|b, C)$ is a Gaussian distribution in vector a with mean b and covariance C; $I_{NT}$ is the NT×NT identity matrix; $\sigma_r^2$ and $\sigma_e^2$ are scalar parameters which control the overall variance contributed by each kernel; K(l) is an NT×NT non-linear kernel with parameter l and elements defined by $$K(\omega_{ij}, \omega_{qp}|l) \equiv \exp\left(-\frac{\|\omega_{ij} - \omega_{qp}\|}{2l^2}\right).$$

An identity matrix of size n is a n×n square matrix with ones on the main diagonal and zeros elsewhere. It is denoted by $I_N$, or simply by I if the size is immaterial or can be trivially determined by the context. The non-linear kernel K may be an RBF kernel in some implementations. The parameter may be a length-scale parameter that determines the overall scale on which the trait varies within an individual subject. For very rapidly varying traits, the length-scale parameter is small (e.g., less than a threshold value) and for slowly varying traits, the length-scale parameter is large (e.g., greater than a threshold value).

The RBF kernel models the dependence in the function domain and subjects while the identity kernel models the remaining environmental noise. Note that the RBF kernel here models not only correlation between function domain points within a subject but also equally across subjects. The RBF kernel behaves in such a way because it can be assumed that the trait at function domain point t is more correlated across subjects i and j than between function domain points t and t+$t_0$ for the same subject (where $t_0$ is an offset in time). For example, person A's height at three years of age is more correlated with person B's height at three years of age then it is with person A's height at 23 years of age. While at first this may seem a counterintuitive choice, it is correct for the types of traits that can be represented as a smoothly-varying function. Traits that can be represented as a smoothly-varying function include, but are not limited to, traits that are the same across all subjects in an analysis, other than by virtue of noise. If a group of subjects includes a trait that cannot be represented as smoothly-varying function, the group of subjects may be divided into one or more sub-groups in which all subjects in a sub-group can all be represented by a smoothly-varying function. This sub-group may be a group of subjects that have the same allele. Examples of such traits include growth curves where on average the curves look the same for individuals within a species, but with a particular SNP mutation the curve changes trajectory. An example where this may be an unreasonable assumption would be un-aligned electrocardiographic signals where no two subjects would in general look the same at time t unless the two signals had been re-scaled and aligned. When the assumption of correlation in the function domain between subjects is not believed to be reasonable, this restriction can be removed from the model, leaving function domain correlations only within a single subject (e.g., person A's height at three years of age is more correlated with person A's height at 4 years of age then it is with person A's height at 23 years of age). As explained below, it is algebraically and computationally trivial to make such change while retaining all efficient computations. However, by removing the assumption of correlation between function domain points across subjects from the model, there is a loss of statistical power if the assumption is actually valid for the data. In the synthetic experiments described below, removal of this assumption in the model weakened the results.

For simplicity, covariates such as age and gender are treated as if they have been regressed out of the trait ahead of time, although any covariate could easily be incorporated in to the model, by way of the Gaussian mean (i.e., fixed effects). All remaining expositions can be readily extended to having covariates directly included with no change to the computational time complexity. Population structure and family relatedness can also be regressed out using either principle components, linear mixed models, or they can be incorporated directly into the RBF kernel. Finally, in Equation 1 there is no assumption that traits for each subject were measured at the same function domain points or that all trait values were included. However, assuming that traits were measured at the same function domain points and that no trait values were missing provides for more efficient computations as discussed below.

The null model 214 described above is generalized to create an alternative model 216 that assumes that genetics do affect a trait and is capable of handling a wide range of genetic effects. One version of the alternative model 216 uses a different model for each allele for a particular SNP. This is referred to as the Partitioned GP model. The Partitioned GP model includes a separate GP regression for each partition of the data, where the partition is defined by the alleles of the test SNP. A more general version of the alternative model 216 has the null model 210 nested within and therefore yields calibrated p-values and a larger power gain. This is referred to as the Unified GP model. In the Unified GP model, the partitions of the Partitioned GP model are all placed within a single Gaussian, with correlation parameters for each pair of alleles dictating how similar the GP regression for each allele should be. The parameters may be varied to make treatment of the different alleles arbitrarily similar or different. Thus, the Unified GP model is more flexible than the Partitioned GP model, which insists that the partitions all be different even when they are not. When these parameters are all equal to one, the Unified GP model is the same as the Partitioned GP model. When these parameters are all zero, the Unified GP model becomes the null model, thereby making it nested inside of the alternative. Additionally, the Unified GP model allows data to be shared across alleles making the computation potentially more statistically efficient.

The partitions in the Partitioned GP model, S, may be represented by s=0, 1, 2 where the number is the number of mutant alleles across the two chromosomes. Thus, the Partitioned GP model is shown by equation 2, $$M_A: p(Y) = \Sigma_{S=1}^S \mathcal{N}((Y_S)|0, \sigma_{r_S}^2 K(W,W|l) \otimes J_{N_S} + \sigma_e^2 I_{N_S T}) \quad (2)$$

where S denotes the number of alleles in the SNP encoding, $Y_S$ is the subset of trait data for which the individual has SNP value s, and where $N_S$ is the number of such individuals. It is possible to use a different length scale l and variance parameters $\sigma_e^2$ for each partition s. However, using the same length scale l and variance parameters $\sigma_e^2$ for each partition s yields good results and allowed testing of SNPs with much lower minor allele frequency (MAF) owing to the data sharing offered by the shared parameters. Much lower MAF may be frequency below a predefined threshold such as, for example, 5%, 1%, or 0.1%. MAF refers to the frequency at which the least common allele occurs in a given population. It may appear that this parameter tying coerces the trait to look the same across SNP partitions, but the effect of sharing parameters only loosely coerces broad properties of the trait to be similar (e.g., scale on which the signal changes). Because GP regression is a non-parametric model, the SNP data 212 itself plays a large role in determining the posterior distribution of functional forms; it is for this reason that model presented in this disclosure is able to capture different functional forms even with tied parameters. The number of partitions can be increased to accommodate epistatic tests wherein combinations of SNPs are tested rather than a single SNP. In this case, each partition would correspond to the value of each of two (or more) SNPs.

The same efficient computations outlined earlier for the null model 214 can be applied equally to this alternative model 216. Therefore, the time complexity of computing the alternative model likelihood has as an upper bound, which is that of the null model. This upper bound is reached only when all subjects are assigned to the same partition. Note too that the null model 214 can be computed just once and then cached across all SNPs tested for increased efficiency.

Beyond data sharing across partitions by virtue of shared parameters, the alternative model 216 has good statistical efficiency owing to the fact that GPs operate in the kernel space where the number of parameters does not depend on the number of function domain points. As few as seven samples per partition is sufficient for achieving statistical efficiency, which with cohort sizes in the tens if not hundreds of thousands, imposes little restriction on the MAF.

A model modification module 218 alters implementation of the null model 214 and the alternative model 216 to reduce computational time and memory needed for fitting the SNP data 212 to the models 214, 216. Memory refers to the data storage consumed in performing a given task, whether primary (e.g., in RAM) or secondary (e.g., on a hard disk drive) and computational time refers to the time consumed in performing a given task, whether particularly in computation or in general response time. A time-memory tradeoff is therefore a case where an algorithm or program trades one of increased memory usage or increased computational time for the other. The utility of a given time-memory tradeoff is affected by related fixed and variable costs (of, e.g., CPU speed, RAM space, hard-drive space), and is subject to diminishing returns. However, modifications to the models 214, 216 disclosed herein improve efficiency in terms of both computational time and memory usage. Absent the modifications described below, a naive implementation of the models 214, 216 would simply concatenate all the data for all the subjects over all the function domain points into one large vector.

In order to obtain a p-value by way of statistical testing the maximum likelihood parameters of the models 214, 216 are estimated multiple times, once per SNP genetic marker. In general, for a fixed set of data and underlying statistical model, the method of maximum likelihood selects the set of values of the model parameters that maximizes the likelihood function. Intuitively, this maximizes the "agreement" of the selected model with the observed data, and for discrete random variables it indeed maximizes the probability of the observed data under the resulting distribution. GP regression models are generally considered computationally expensive statistical models. Computing the maximum likelihood across all of the SNP variations for the null and alternative hypothesizes is a non-trivial goal in the sense that general kernel-based methods have time complexity which scales cubically in the dimension of the kernel (here NT), and memory usage which is quadratic in that dimension. The complexity is based on the number of unique measurements so complexity is determined by the number of subjects multiplied by the number of times data was sampled. Thus, the increasing prevalence of wearable, and other, devices combined with the ability of these devices to frequently measure a trait, can result in a very large number of unique measurements. However, this disclosure identifies ways in which structure in the kernel can be leveraged to gain substantial advantages in both computational time and memory usage. Two techniques for reducing computational time and memory usage include decomposing the covariance term into a Kronecker product 220 and approximation of the desired module using pseudo-observations and variational inference 222.

When there is no missing data and all traits are measured at the same function domain points for all subjects, the likelihood can be re-written with Kronecker products 220 in the covariance term, yielding dramatically reduced computational time and memory requirements. This approach requires no approximation and does not require unrolling the matrix. For this approach, the non-linear kernel (dimension NT×NT in Equation 1) is a specially structured kernel because of the repeating function domain points across subjects. For example, if the function domain is time and all patients in a clinical trial have characteristics of a trait measured at days 1, 3, 7, 14, and 28 in the clinical trial then all values for the trait can be aligned across all patients at the common measurement times. Stated differently, it is possible to exploit regularity in the structure of the data related to the values of a trait measured across the function domain (e.g., regular measurements over time, constant thickness of MRI image slices, etc.). This structure makes it possible to re-write the Gaussian likelihood for the null model 214 as shown in Equation 1 in matrix-variate form as shown in Equation 3, $$M_0: p(Y) = N((Y)|0, \sigma_r^2 K(W,W|l) \otimes J_N = \sigma_e^2 I_{NT}) \qquad (3)$$

where K(W,W|l) is overloaded to now indicate a T×T matrix, and where $J_N$ is the square matrix of all ones of size N. The symbol ⊗ denotes the Kronecker product 220 which produces a square matrix of dimensions ab×ab for A⊗B if A and B are square matrices of dimension a and b respectively. The Kronecker product 220 is an operation on two matrices of arbitrary size resulting in a block matrix. It is a generalization of the outer product (which is denoted by the same symbol) from vectors to matrices, and gives the matrix of the tensor product with respect to a standard choice of basis. The computational time complexity of evaluating the likelihood in Equation 1 is $O(N^3 T^3)$ because solving the equation includes computing the inverse and determinant of the covariance matrix of dimension NT×NT. In contrast, using a spectral-decomposition-based re-factoring as shown by Equation 3, the computational time complexity is reduced to $O(T^3)$. If $J_N$ were an arbitrary matrix the time complexity would be $O(N^3+T^3)$, but because the spectral decomposition of $J_N$ can be computed once and cached, the complexity becomes $O(T^3)$. Moreover, because it is an all-ones matrix, its spectral decomposition can be computed more efficiently than in the general case. In particular, by defining $U_r S_r U_r^T$ as the spectral decomposition of the T×T matrix K(l), and $U_r S_r U_r^T$ as the spectral decomposition of $J_N$, the log likelihood of the null model can be rewritten as shown here in Equation 4:

$$\mathcal{L}_0 = \qquad (4)$$
$$-\frac{NT}{2}\ln(2\pi) - \frac{1}{2}\ln|S_r \otimes S_j| - \frac{1}{2}vec(U_r^T Y U_j)^T (S_r \otimes S_j)^{-1} vec(U_r^T Y U_j).$$

Equation 4 and its derivative can be generalized to account for data when the mean of the Gaussian is non-zero without any added time or space complexity. Avoiding addition of time or space complexity allows the processing to remain computationally efficient and able to be processed faster that other techniques that would increase time or space complexity.

Note that the subjects are not identically and independently distributed (iid) in the null model because of the term $J_N$. If $J_N$ is replaced with the identity matrix, then the subjects would be iid, which thus amounts to relaxing the assumption that the function domain points across subjects are correlated. Also, instead of assuming that population structure and family structure have already been accounted for, population structure and family structure could instead be incorporated into the model by adding to $J_N$ a genetic similarity matrix, incurring a time complexity of $O(N^3+T^3)$ in the most general case.

For parameter estimation when there is no missing data and all traits are measured at the same function domain points for all subjects, an optimization routine is used to obtain the maximum likelihood solution in parameters l, $\sigma_r^2$, $\sigma_e^2$ (all scalars). In some implementations, the optimization routine may be a second order method such as a quasi-Newton method, conjugate gradient, gradient descent, etc. Quasi-Newton methods are methods used to either find zeroes or local maxima and minima of functions, as an alternative to Newton's method.

Newton's method is an iterative method for finding the roots of a differentiable function $f$ (i.e. solutions to the equation $f(x)=0$). In optimization, Newton's method is applied to the derivative $f$ of a twice-differentiable function $f$ to find the roots of the derivative (solutions to $f'(x)=0$), also known as the stationary points of $f$. Examples of quasi-Newton methods include Broyden-Fletcher-Goldfarb-Shanno (BFGS) algorithm. In numerical optimization, the BFGS algorithm is an iterative method for solving unconstrained nonlinear optimization problems. The BFGS method approximates Newton's method, a class of hill-climbing optimization techniques that seeks a stationary point of a (preferably twice continuously differentiable) function. For such problems, a necessary condition for optimality is that the gradient be zero. The BFGS method may be implemented as limited-memory BFGS (L-BFGS or LM-BFGS) to use less computer memory. Like the original BFGS, L-BFGS uses an estimation to the inverse Hessian matrix to steer its search through variable space, but where BFGS stores a dense n×n approximation to the inverse Hessian (n being the number of variables in the problem), L-BFGS stores only a few vectors that represent the approximation implicitly. Due to its resulting linear memory requirement, the L-BFGS method is particularly well suited for optimization problems with a large number of variables. Instead of the inverse Hessian $H_k$, L-BFGS maintains a history of the past m updates of the position x and gradient $\nabla f(x)$, where generally the history size m can be small (often m<10). These updates are used to implicitly do operations requiring the $H_k$-vector product.

Newton's method and the BFGS methods are not guaranteed to converge unless the function has a quadratic Taylor expansion near an optimum. These methods use both the first and second derivatives of the function. However, BFGS has proven to have good performance even for non-smooth optimizations. The scalars l, $\sigma_r^2$, $\sigma_e^2$, are real numbers and relate to vectors in a vector space through the operation of scalar multiplication, in which a vector can be multiplied by a number to produce another vector. Because the log likelihood is not convex, it is possible to perform empirical tests using multiple random re-starts. Five restarts yields good results in empirical tests.

When there are uneven function domain points or missing data it is still possible to achieve computational speed-ups using Partitioned GP if some approximations are made with variational inference 222. In a model with a vector Gaussian likelihood, such as Equation 1, missing trait data can be handled by removing any rows with missing data, because this procedure is equivalent to marginalization in a Gaussian. In such a manner, if using Equation 1, T could represent the number of uniquely observed function domain points across all subjects, even if many subjects were missing many of these function domain points. This procedure could also capture the case where different subjects were measured at different function domain points. However, in the Kronecker version of the likelihood written for computational efficiency gains (Equation 3), it is not possible to perform this arbitrary marginalization by simply removing an element of the phenotype vector. With the Kronecker-factorized covariance matrix it would be necessary to remove all subjects missing a time point or remove all function domain points missing a subject. Therefore, alternative formulations and/or approximations are used to achieve computational efficiency when there is missing data.

Specifically, the Gaussian likelihood is kept in vector form (as in Equation 1 rather than rewritten with Kronecker products as in Equation 3), and augmented with latent inducing inputs, which are points in the smoothly-varying variable (e.g., time or space) that are included in the model. Inducing inputs is referred to as "pseudo-observations" in time (or space) that are included in the non-linear kernel inputs; when conditioned on, these pseudo-observations make any observed data conditionally independent of each other. The pseudo-observations take the same form as actual observations but do not exist in the data. Use of pseudo-observations has the effect of reducing the time complexity from $O((NT)^3)$ in Equation 1 to $O(NTQ^2)$ for Q inducing inputs. In such a variational approach, only the number, not location, of pseudo-observations are specified. The locations are learned as part of the parameter estimation procedure. By varying the number of pseudo-observations it is possible to control the relative time complexity and level of approximation. For many functions describing behavior of a trait, it is not necessary to use all the available data points to understand the function. Also note that if the number of pseudo-observations equals the number of uniquely observed function domain points, then there is no longer any approximation and the algorithm is exact. In the Partitioned GP model with three partitions (based on alleles) the pseudo-observations can be shared across partitions further reducing computational time and increasing statistical power. This is one approach to gaining computational efficiency when characteristics of a dataset prevent use of the Kronecker product approach.

A model comparison module 224 compares the likelihood of the SNP data 212 fitting the null model 214 and likelihood of the SNP data 212 fitting the alternative model 216. The likelihood of the null model 214 could be found by Equation 1 or a modification of that equation. The likelihood of the alternative model 216 could be found by Equation 2 or a modification of that equation. Optimization is achieved by finding the two likelihoods. Once found, the model comparison module 224 identifies which of the two models 214, 216 best explains the data for a given SNP by determining which likelihood is higher. A higher likelihood indicates a better fitting model. This may be repeated for each tested SNP. If the model comparison module 224 determines that the likelihood of the data fitting the alternative model is higher than the likelihood of the data fitting the null model, it can be concluded that the trait is more likely to be correlated with the SNP. By repeating this across multiple SNPs it is possible identify which are likely to be correlated with the trait and which are not. After generating results, the model comparison module 224 may send an indication of the results to the network connector(s) 208 for delivery to a different computing device and/or to the input/output components for displaying locally on the computing device(s) 110.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations is modified or omitted.

Figure 3:
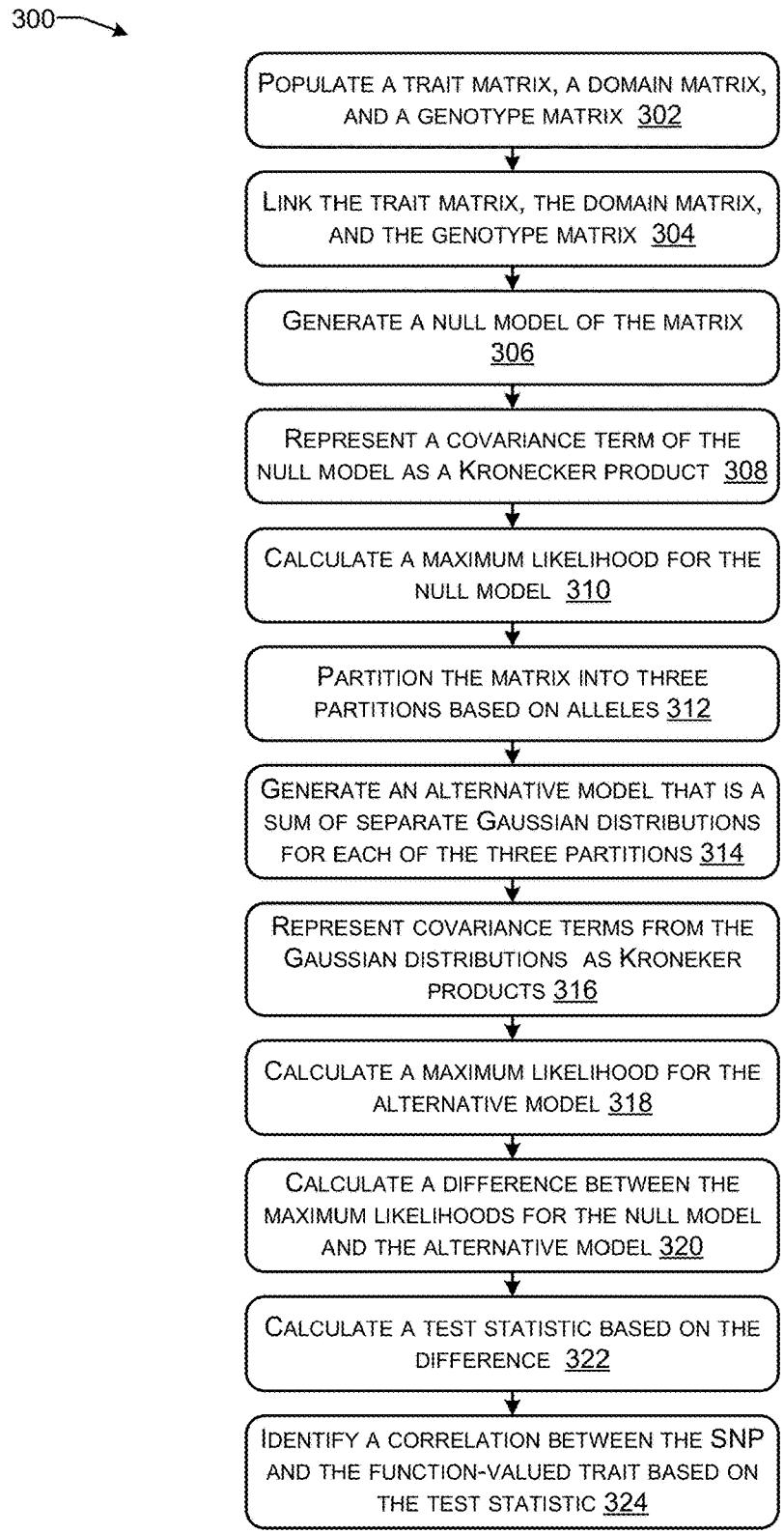
FIG. 3 shows an illustrative process for using a partitioned GP regression to identify correlations between SNPs and traits.

FIG. 3 shows an illustrative process 300 for identifying a correlation between a single-nucleotide polymorphism (SNP) and a function-valued trait in genome-wide association study (GWAS) in a computationally-efficient manner.

At 302, a trait matrix of values of the function-valued trait, a domain matrix with values of a plurality of function domain points, and a genotype matrix with variations in alleles of the SNP are, for a plurality of subjects at a plurality of function domain points, populated. This matrix may be an N×T matrix where N represents the subjects and T represents the function domain points. Thus, for a clinical study of 100 people in which the trait was measured 12 times for each person, the matrix would be a 100×12 matrix. The function domain points are points where the trait is observed across the domain over which the trait is smoothly varying. For example, the domain may be time and the trait may be LDL cholesterol levels. LDL cholesterol levels do not change from 130 mg/dL to 150 mg/dL without being 140 mg/dL at some point. Thus, the trait of LDL cholesterol level is an example of a trait which is smoothly varying over time.

At 304, the trait matrix, the domain matrix, and the genotype matrix may be linked.

At 306, a null model is generated. The null model includes a Gaussian distribution of the matrix with mean value and a first covariance term determined in part by a non-linear kernel applied to the domain matrix and in part by a first parameter. In some implementations the mean value is zero. The first covariance term is defined in part by a first covariance matrix. The non-linear kernel may be implemented as a RBF kernel. The first parameter may comprise a length-scale parameter. The same kernel function is used to calculate the alternative function.

At 308, the first covariance term of the null model is represented as a Kronecker product. Decomposition of the covariance term into a Kronecker product reduces computational time and memory needed to calculate a maximum likelihood for the null model.

At 310, a maximum likelihood is calculated for the null model. The maximum likelihood may be calculated by the model comparison module 224.

At 312, the matrix is partitioned into three partitions based on alleles of the SNP. Data in the matrix will be associated with one of the three alleles for the SNP: homologous wild type, heterozygous, or homologous mutant. Therefore, each of the partitions includes data from a separate subset of the subjects grouped by common alleles.

At 314, an alternative model is generated. The alternative model sums together Gaussian distributions of each of the three partitions of the matrix with mean value and a second, third, and fourth covariance term determined in part by a second, third, and fourth non-linear kernel, where the kernel is determined by a kernel function applied to a respective one of the three partitions of the matrix and a second parameter. The kernels are different for each of the partitions, but all are determined by the same kernel function. The second parameter may comprise a length-scale parameter. In some implementations, the mean value may be zero.

In one implementation, the second covariance term is defined in part by a second covariance matrix, the third covariance term is defined in part by a third covariance matrix, and the fourth covariance term is defined in part by a fourth covariance matrix, all of which define similarities across subjects based in part on population structures or the family structures. A same kernel function is used to compute each of the matrices from the corresponding partition (i.e., the kernel function used to compute the second covariance matrix from the first partition is the same kernel function used to compute the third covariance matrix from the second partition). A kernel function describes how to compute the $(i,j)^{th}$ entry of a covariance matrix given input vectors x_i and x_j corresponding to data (e.g., function domain values) from the $i^{th}$ and $j^{th}$ individuals. Application the same kernel function to different subjects (thus different sets of data), results in different matrices that may be of different size and with different actual values.

At 316, the second, third, and fourth covariance terms are represented as a second, third, and fourth Kronecker product.

At 318, a second maximum likelihood is calculated for the alternative model. The maximum likelihood may be calculated by the model comparison module 224.

At 320, the difference is calculated between the maximum likelihood for the null model and the maximum likelihood for the alternative model. The difference may be calculated by the model comparison module 224.

At 322, a test statistic is calculated based on the difference. The test statistic may be based on a chi-squared test. Chi-square is distribution used to assess statistically the goodness of fit of a model to observed data. In chi-squared tests, the sampling distribution of the test statistic is a chi-square distribution when the null hypothesis is true.

At 324, existence of a correlation between the SNP and the function-valued trait is identified based on the test statistic. The correlation identifies that genetic variation in the SNP is associated with, but not necessarily causal for, changes in the function, which describes behavior of the function-valued trait.

Figure 4:
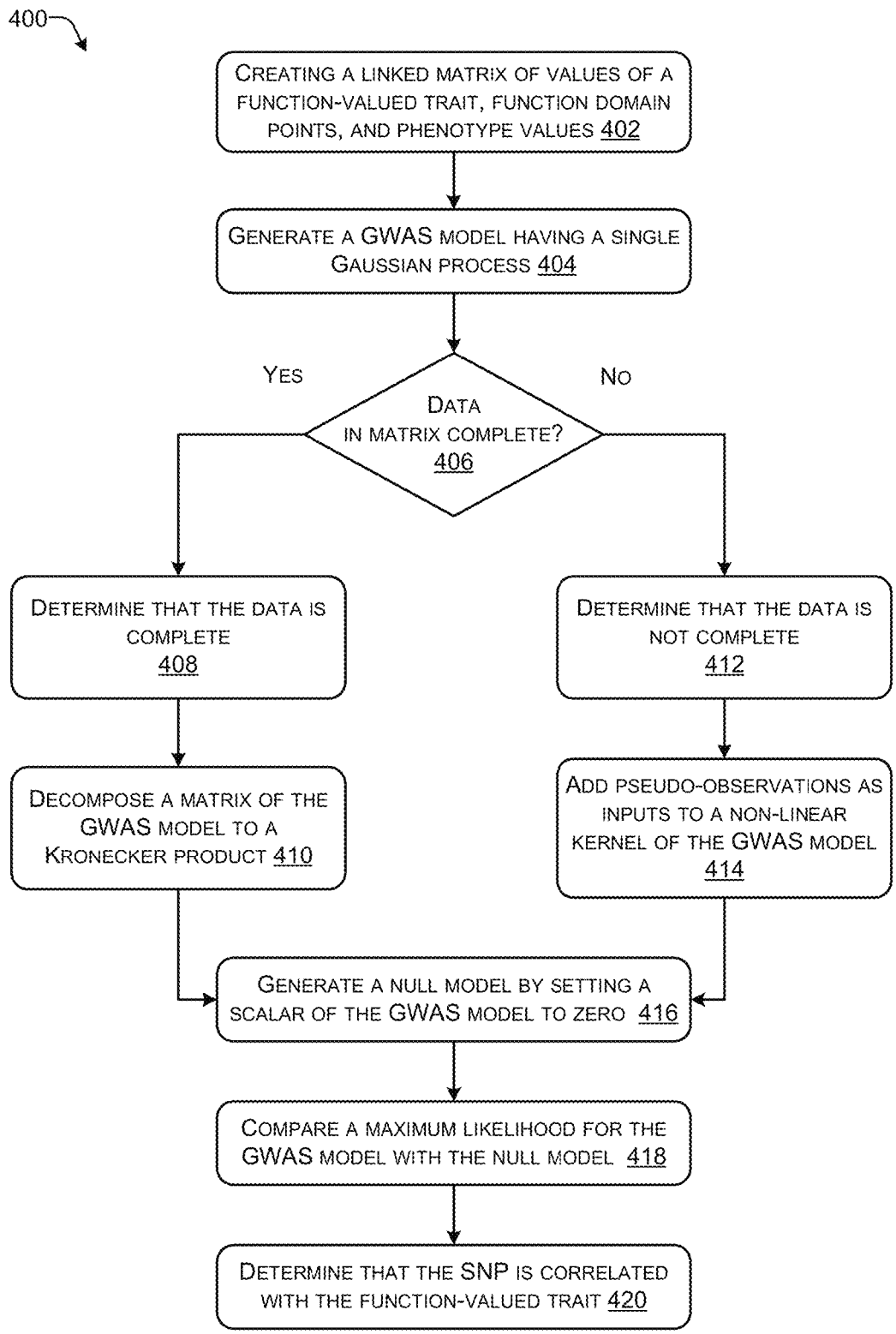
FIG. 4 shows an illustrative process for using a nested GWAS model to identify correlations between SNPs and traits.

FIG. 4 shows an illustrative process 400 for identifying a correlation between a single-nucleotide polymorphism (SNP) and a function-valued trait in genome-wide association study (GWAS) in a computationally-efficient manner.

At 402, a linked matrix of values of the function-valued trait, values of function domain points, and genotype values for each allele combination of the SNP is created. This matrix may be an N×T matrix where N represents the subjects and T represents the function domain points. Thus, for a clinical study of 100 people in which the trait was measured 12 times for each person, the matrix would be a 100×12 matrix. The function domain points are points where the trait is observed across the domain over which the trait is smoothly varying. This matrix includes data for all three allele combinations of the SNP: homologous wild type, heterozygous, or homologous mutant.

At 404, a GWAS model is generated. The GWAS model as a single Gaussian process of a vector derived from the linked matrix, and a covariance based upon at least one scalar and a non-linear kernel. The Gaussian process includes a mean value which may be zero or a non-zero value. The non-linear kernel may be a RBF kernel or a Matern kernel. The scalar comprises a correlation parameter for each pair of alleles of the SNP indicating a degree of trait similarity between the data with each allele in the pair. The GWAS model may also include a parameter that determines an overall scale on which the function-valued trait varies as a function varies.

At 406, is determined if the data that makes up the matrix is complete, that is it is free from any missing values, and if the data is aligned across the plurality of subjects. The data may be aligned if it is collected at the same function domain point for each subject. For example, data collected every day for each subject is aligned. All subjects have day 1 data, day 2 data, day 3 data etc. The data may also be aligned if function domain points of the data from each subject may be matched with function domain points from the data of the other subjects. For example, electrocardiogram data will have a peak for each heartbeat for each subject. The heartbeats across all the subjects did not occur at the same times, the peaks on the electrocardiogram data can be aligned so that each subject has data representing heartbeat #1, heartbeat #2, heartbeat #3, etc.

Data that is not aligned can be treated as data that has missing values. For each function domain point which has values for less than all of the subjects (i.e., due to the lack of alignment) the subjects for which there is no value can be treated as having missing data. Thus, unaligned data can be handled as a case of missing data. If the data is both complete and aligned, process 400 proceeds to 408 where it is determined that there are no missing data in the values of the function-valued trait.

At 410, at least part of the covariance term of the GWAS model is decomposed to a Kronecker product thereby reducing computational time and memory needed to calculate a maximum likelihood for the alternative model. Decomposition of the covariance into a Kronecker product reduces computational time and memory needed to calculate a maximum likelihood for the alternative model.

If, however, the data is not complete, process 400 proceeds to 412 where the missing values of the function-valued trait are marginalized. Function domain points that are not aligned may be handled by treating them as being aligned but having missing values for some of the domain points.

At 414, pseudo-observations are added as inputs to the non-linear kernel thereby making the values of the function-valued trait conditionally independent and reducing time complexity for maximizing a lower bound of the first likelihood and a lower bound of the second likelihood.

At 416, a null model is generated from the GWAS model by setting a value of the at least one scalar to zero. Because the null model can be generated by setting a value of the GWAS model to zero, the null model is nested within the alternative model (i.e., the GWAS model).

At 418, a maximum likelihood for the GWAS model and a maximum likelihood for the null model are compared. Comparing maximum likelihoods for both models for a given SNP indicates whether it is more probable that changes in the trait correlate with genetic variations in the SNP or more probable that changes in the trait do not correlate with genetic variations in the SNP.

At 420, it is determined that the SNP is correlated with the function-valued trait because the maximum likelihood for the GWAS model is higher than the maximum likelihood score the null model. The determining may proceed by using a test statistic such as a chi-squared test.

Examples

Many models have been developed to perform GWAS with function-valued traits. However, these other models have constraints on the type of genetic or time effect that can be recovered (e.g., only constant or linear effect in time, or only linear in the SNP). The Partitioned GP model described above does not suffer from those limitations. Computational efficiency also limits other models to relatively few function domain points because the number of parameters scales with the number of function domain points thus preventing calculation of a large number of function domain points (as is expected for function-valued traits) in a reasonable amount of time.

The examples provided herein use synthetic datasets (so that the true characteristics of the relationships between SNPs and traits are known) to compare the behavior of the Partitioned GP model to a set of baseline models. The examples explore what happens when there is a large number of function domain points (specifically time points because the function domain is time) such as would be collected be wearable devices and other situations that results in frequent observation of phenotypic traits. The models are called Partitioned GP, Furlotte, Inverse linreg (linear regression), and Inverse K (Kernel) score.

Partitioned GP is the model described above in this disclosure. For testing, the (exact) Kronecker product implementation as shown by Equations 2 and 4 was used. Furlotte is a linear mixed model described in Nicholas A. Furlotte, Eleazar Eskin, and Susana Eyheramendy. Genome-wide association mapping with longitudinal data. *Genetic Epidemiology*, 36(5):463-471, 2012. In Furlotte, correlation in time is modelled using an auto-correlation kernel (an RBF was selected for closer comparison to Partitioned GP), and where in the alternative model, the SNP is limited to producing a fixed effect which shifts values for the trait at all function domain points by the same amount. A standard likelihood-ratio test (LRT) is used for the one-degree-of-freedom test. Inverse linreg is a relatively standard model to use for examining how the number of parameters increases with the number of function domain points. However, Inverse linreg does not scale well and has difficult when there are more than 50 function domain points. Inverse K score is a modification of Inverse linreg where the time-effects are integrated out, yielding a linear mixed model. In this way, the number of parameters in the Inverse K score model does not depend on the number of function domain points. Thus, Inverse K score addresses some of the deficiencies of the Inverse linreg model. The SNP was modelled as the dependent variable and each trait in time was an independent variable. Testing was done with a $\chi^2$ test with T degrees of freedom (total number of function domain points, assumed the same for all subjects). Inverse K score is a model that may be thought of as a Bayesian equivalent to A score test was used to obtain a p-value.

Each of these modes was tested on simulated phenotypic data to examine type I error control, statistical power, and ability to rank hypotheses regardless of calibration. The simulated data is based on the actual SNP data publically available in the CARDIA data set (dbGaPphs000285.v3.p2) which, was filtered to remove subjects missing more than 10% of their SNPs, any SNPs missing more than 2% of the subjects, and any SNPs with MAF of less than 5%. This left 1,441 subjects with 540,038 SNPs. The only covariate is an off-set, which is regressed as a pre-processing step before applying the models. In the examples, it is assumed that basic properties such as the noise level and length-scale are likely to be common to all alleles and hence these parameters are tied together for a more efficient statistical estimation.

Figure 5:
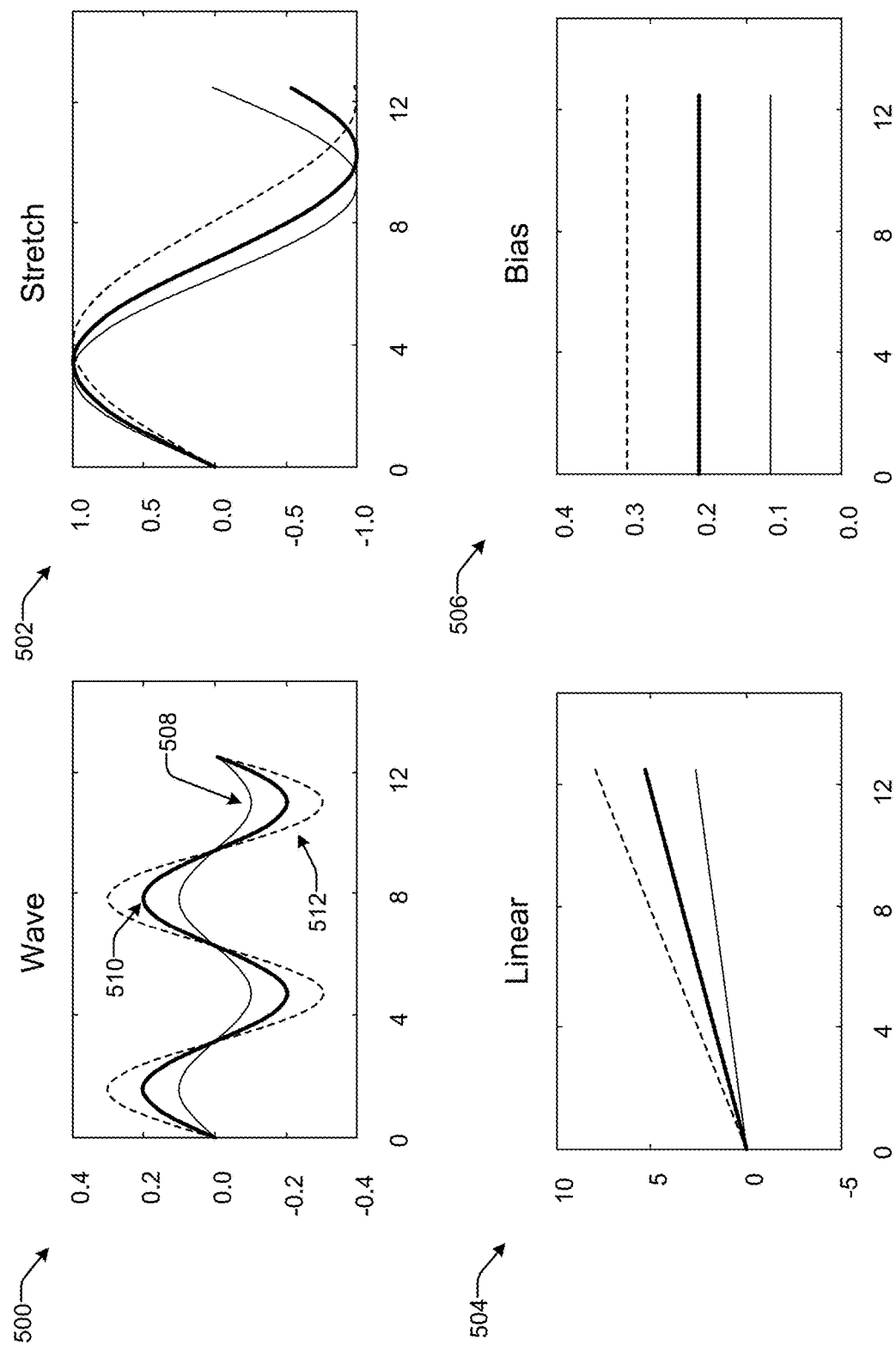
FIG. 5 shows the effects of SNP variations on trait values for simulated traits.

FIG. 5 shows a set of simulated traits and four different genetic effects that the techniques contained in this disclosure are able to detect. Each trait includes 100 time points with values uniformly spaced between 0 and 12. The genetic effects are represented by the functions wave 500, stretch 502, linear 504, and bias 506. For the wave (a sin wave), the amplitude increases as a linear function of the SNP; for the linear (a straight line), the slope changes as a linear function of the SNP; for the bias, the horizontal intercept changes as a linear function of the SNP; and for stretch (a sin wave), the frequency changes as a linear function of the SNP. The thin lines 508 represent trait values when both alleles contain the wild-type SNP. The heavy lines 510 represents trait values when the alleles are heterozygous for the wild-type and mutant SNP. The dashed lines 512 represent trait values when both alleles have the mutant genotype in the SNP. The canonical traits shown in FIG. 5 are not themselves experimental results, but are the datasets that serve as the basis of the experiments described below. In these examples, by design, a model that can only account for a constant genetic effect (e.g., linear in time) will fail to properly model the data across all four type of genetic effects. These traits are idealized representations that present testable criteria for distinguishing between effective and ineffective modeling techniques.

Null data was generated by noisy versions of these four traits where the noise was iid in time and across subjects. The non-null data was the noise-free trait modified in a smoothly varying way as a function of genotype before adding iid noise. Experiments varied both the SNP effect intensities and the amount of noise. The strength of the SNP effect at each time point is summarized by the fraction of variance explained by the genetic signal at each time point (i.e., the variance of the noiseless trait divided by total variance, all at a given time point). Experiments were conducted with 10, 50, 100, and 150 time points.

Partitioned GP was first tested to determine if this technique controls type I error. Because the null and alternative models are not nested, standard frequentist hypothesis testing (which is used for nested models) cannot be used to compute p-values. Two statistical models are nested if the first model can be transformed into the second model by imposing constraints on the parameters of the first model. For example, the set of all Gaussian distributions has, nested within it, the set of zero-mean Gaussian distributions: constraining the mean in the set of all Gaussian distributions to zero yields the zero-mean distributions. However, various forms of permutation testing are available to obtain calibrated p-values for non-nested models.

For example, applying a standard $\chi^2$ test to generate p-values for the alternative model shows that type I error is controlled, albeit extremely conservatively even though the assumptions of the $\chi^2$ test are not met.

The standard $\chi^2$ test is applied to this model by computing the maximum likelihood of the data under the null and under the alternative models, $\mathcal{L}_A$ and $\mathcal{L}_0$, counting the number of degrees of freedom different between them, d, and then applying the standard p-value computation. The null model has no partitions and has three free scalar parameters: $\sigma_r^2$ and l, the overall-variance and length-scale for the time-based kernel, and $\sigma_e^2$ for the residual noise. The alternative model shares all parameters across partitions except for the time-based kernel variances, $\sigma_{r_s}^2$ (one per SNP allele), leading to two more parameters than the null model. These two parameters are considered two extra degrees of freedom even though these two additional parameters are constrained to be greater than zero and so are not truly full degrees of freedom—such miscounting can only lead to overly-conservative p-values in the case of properly nested models. The test statistic is then twice the difference between the null and alternative maximum log likelihoods, $\Delta=2(\mathcal{L}_A-\mathcal{L}_0)$, from which a p-value using a $\chi_d^2$ test with d=2 of freedom is computed. Although this p-value is uncalibrated, it does control type I error as shown in Table 1.

TABLE 1

Control of type I error at significance thresholds for traits with 10 time points using 390,272 tests. Fraction of p-values below that threshold, with absolute numbers in parentheses.

| Model | $\alpha = 10^{-2}$ | $\alpha = 10^{-3}$ | $\alpha = 10^{-4}$ | $\alpha = 10^{-5}$ |
|---|---|---|---|---|
| Partitioned GP | $1.1 \times 10^{-3}$ (434) | $6.7 \times 10^{-5}$ (26) | 0.0 (0) | 0.0 (0) |
| Inverse K score | $9.1 \times 10^{-3}$ (3568) | $8.8 \times 10^{-4}$ (342) | $5.6 \times 10^{-5}$ (22) | $1.0 \times 10^{-5}$ (4) |
| Inverse linreg | $9.8 \times 10^{-3}$ (3828) | $9.4 \times 10^{-4}$ (366) | $6.1 \times 10^{-5}$ (24) | $1.0 \times 10^{-5}$ (4) |
| Furlotte | $9.2 \times 10^{-3}$ (3589) | $9.3 \times 10^{-4}$ (362) | $6.1 \times 10^{-5}$ (24) | $1.5 \times 10^{-5}$ (6) |

To generate the results shown in Table 1, first 8,000 tests were conducted at each of 10, 50, 100, and 150 time points, finding that a smallest number of time points is less conservative than a larger number of time points. Next, larger scale simulations of null-only data for 10 time points were performed, obtaining 390,272 test statistics. Combined, this was just under half a million tests, which provided the resolution to check for control of type I error up to a significance level of $\alpha=10^{-5}$. As can be seen in Table 1, all models control the type I error up to $\alpha=10^{-5}$. Partitioned GP is more conservative at controlling the type I error than the three other models. This could occur at the cost of lower statistical power in a power comparison.

Figure 6:
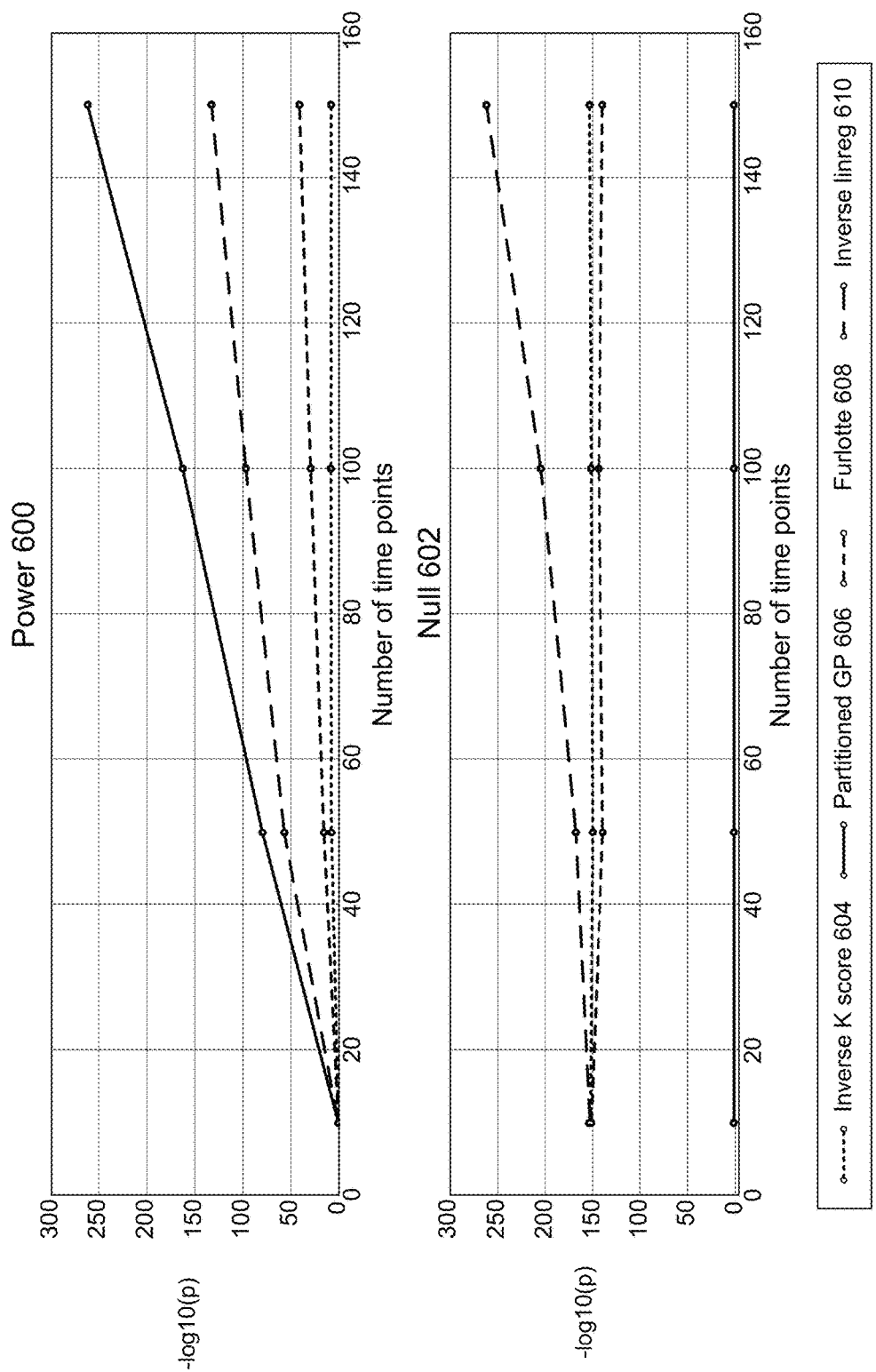
FIG. 6 shows power curves as a function of time for multiple tested models.

FIG. 6 shows that Partitioned GP has more statistical power to detect SNP-trait associations than any of the other three models. FIG. 6 shows the median test statistic as −log(10) p-value for both non-null (upper plot) 600 experiments and null (lower plot) 602 experiments. The null plot 602 is included because the type I error control experiments only went to $\alpha=10^{-5}$. This null plot 602 shows that while the Inverse K score 604 remains calibrated, the inverse linreg (linear regression) 610 becomes inflated, failing to control the type I error. Partitioned GP is extremely conservative in controlling the type I error as shown by Table 1 yet provides the most power as shown by FIG. 6. Note that the Inverse K score 604 test appears to have the lowest power. However, the power plot 600 is perhaps misleading in the sense that the Inverse K score 604 test uses a numerical routine, which has limited precision, yielding many zeros for tiny p-values (usually those smaller than $10^{-8}$). This can be handled by either keeping these values at zero, which would give the Inverse K score 604 test an unfair advantage, or to replace all zero p-values with $10^{-8}$. Power plot 600 was generated by replacing all zero values with $10^{-8}$, thereby showing the model with less power than it may have if there were a way to compute p-values with more precision.

Due to the above limits on directly comparing the Inverse K score 604 test with the other models, a metric that does not depend in any way on calibration and is less sensitive to p-value resolution—Receiver Operating Characteristics (ROC) curves—were used to investigate the ability of each model to discriminate true nulls from alternatives. The ROCs for each model show that the Inverse K score 604 test performs well, though not as well as the Partitioned GP 606. Note that inverse linreg 610, though showing inflated test statistics in the null plot 602, demonstrates in ROCs that it maintains the ability to properly rank the hypotheses from most to least significant, though again, not as well as the Partitioned GP 606. The performance of Furlotte 608 is the least adaptable out of all four models because Furlotte is only able to capture shifts in the mean of the functional trait, not the richer SNP effects tested by these simulations.

Figure 7:
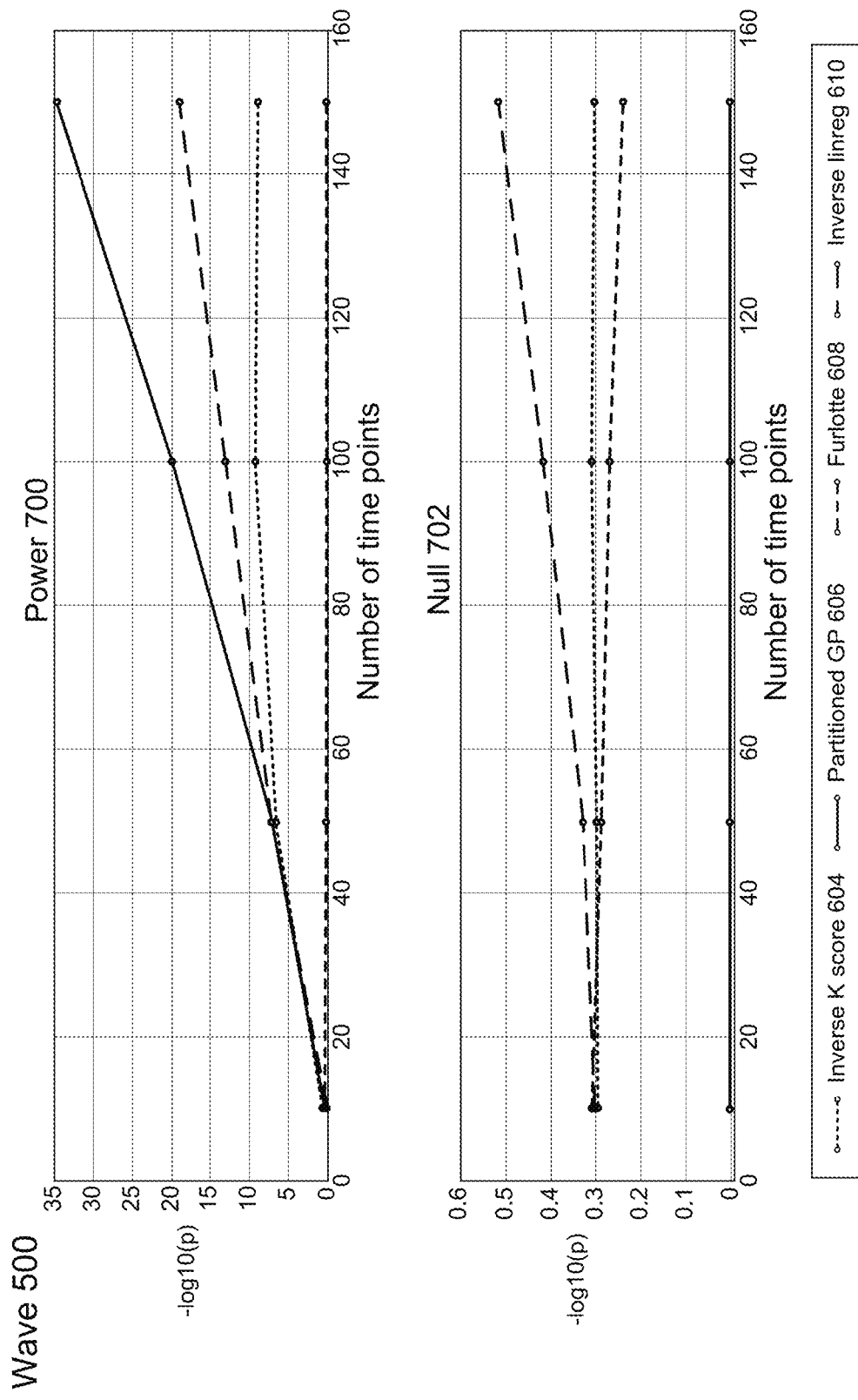
FIG. 7 shows the power curves of FIG. 6 limited to data exhibiting a wave trait.
Figure 8:
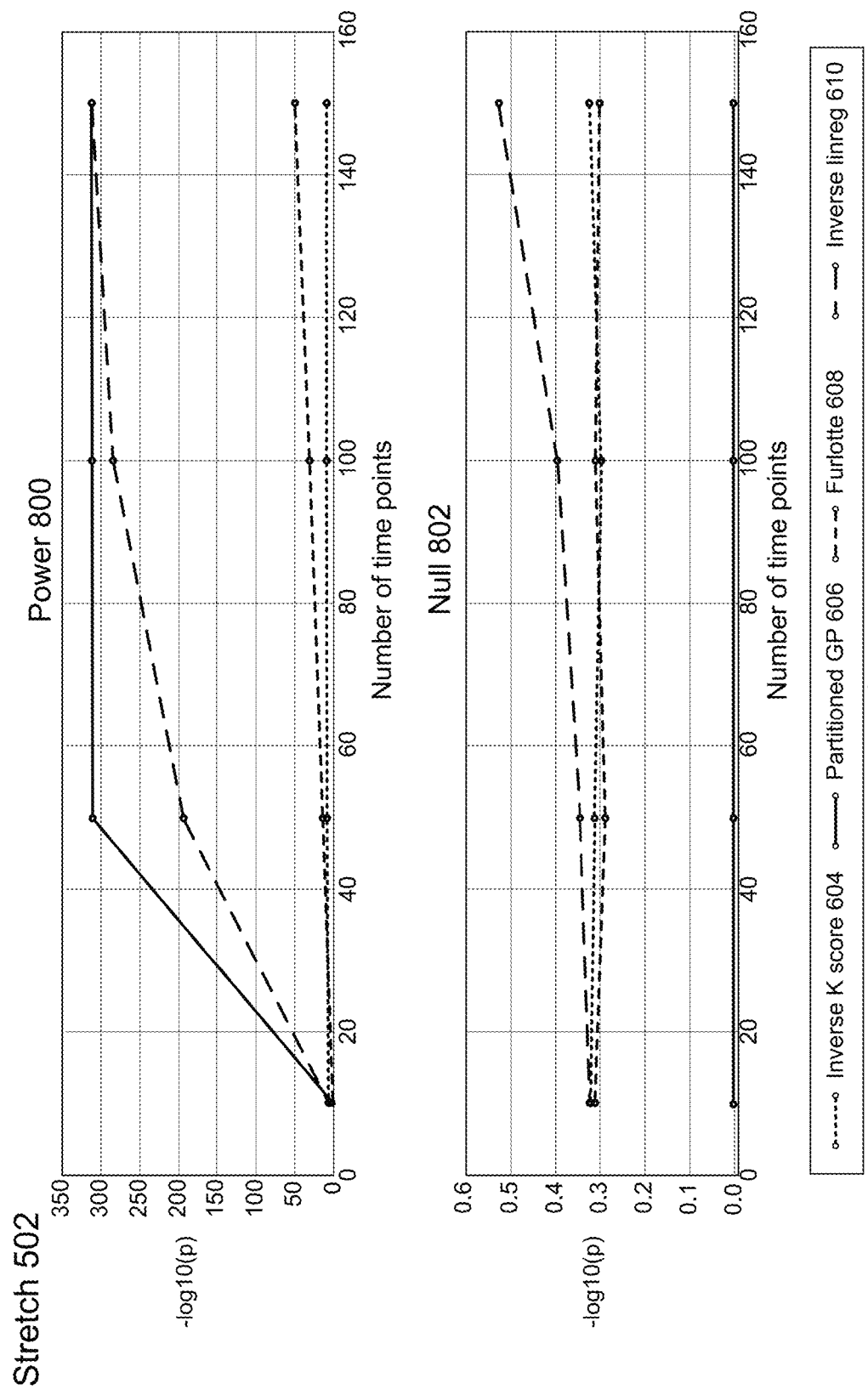
FIG. 8 shows the power curves of FIG. 6 limited to data exhibiting a stretch trait.
Figure 9:
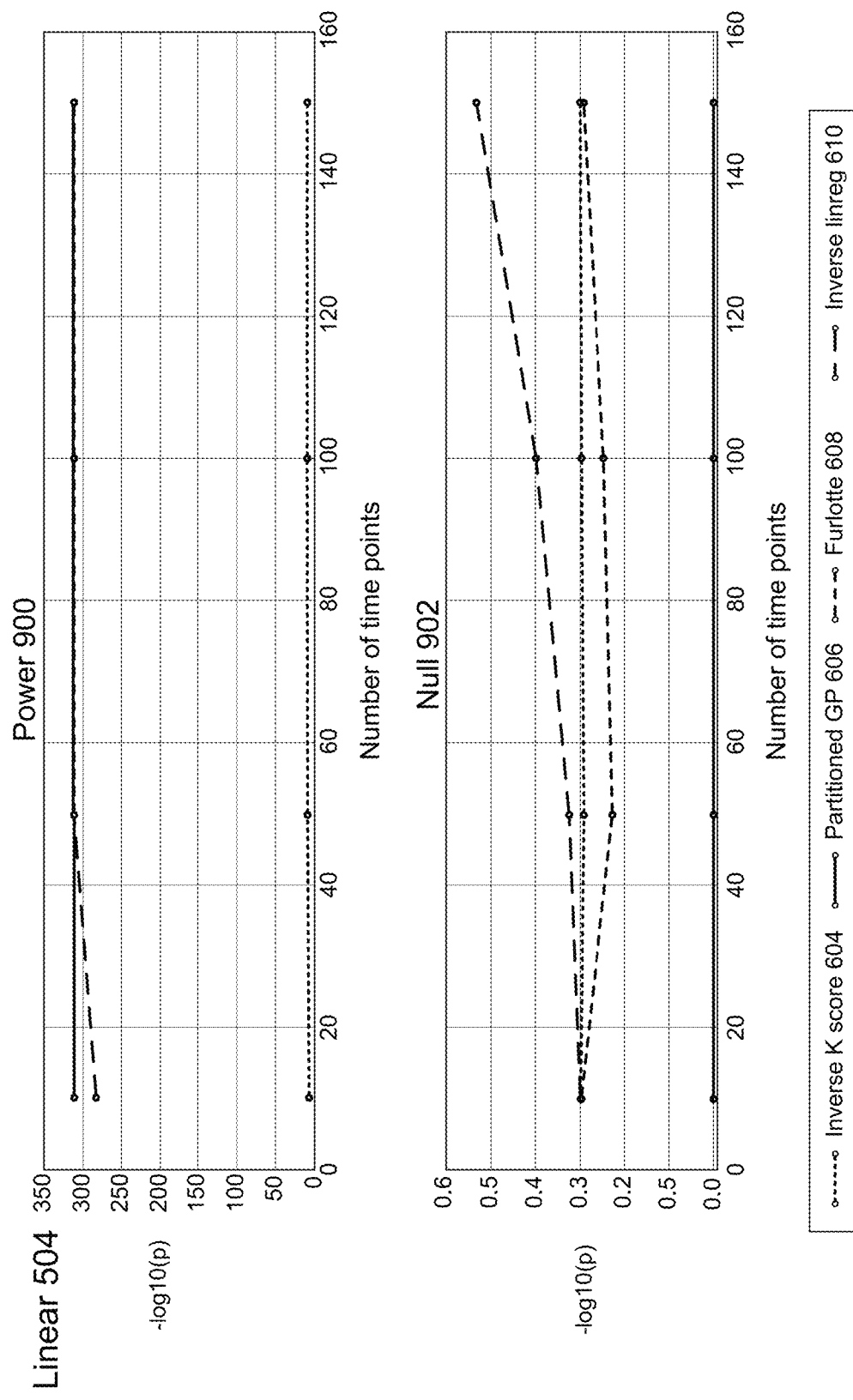
FIG. 9 shows the power curves of FIG. 6 limited to data exhibiting a linear trait.
Figure 10:
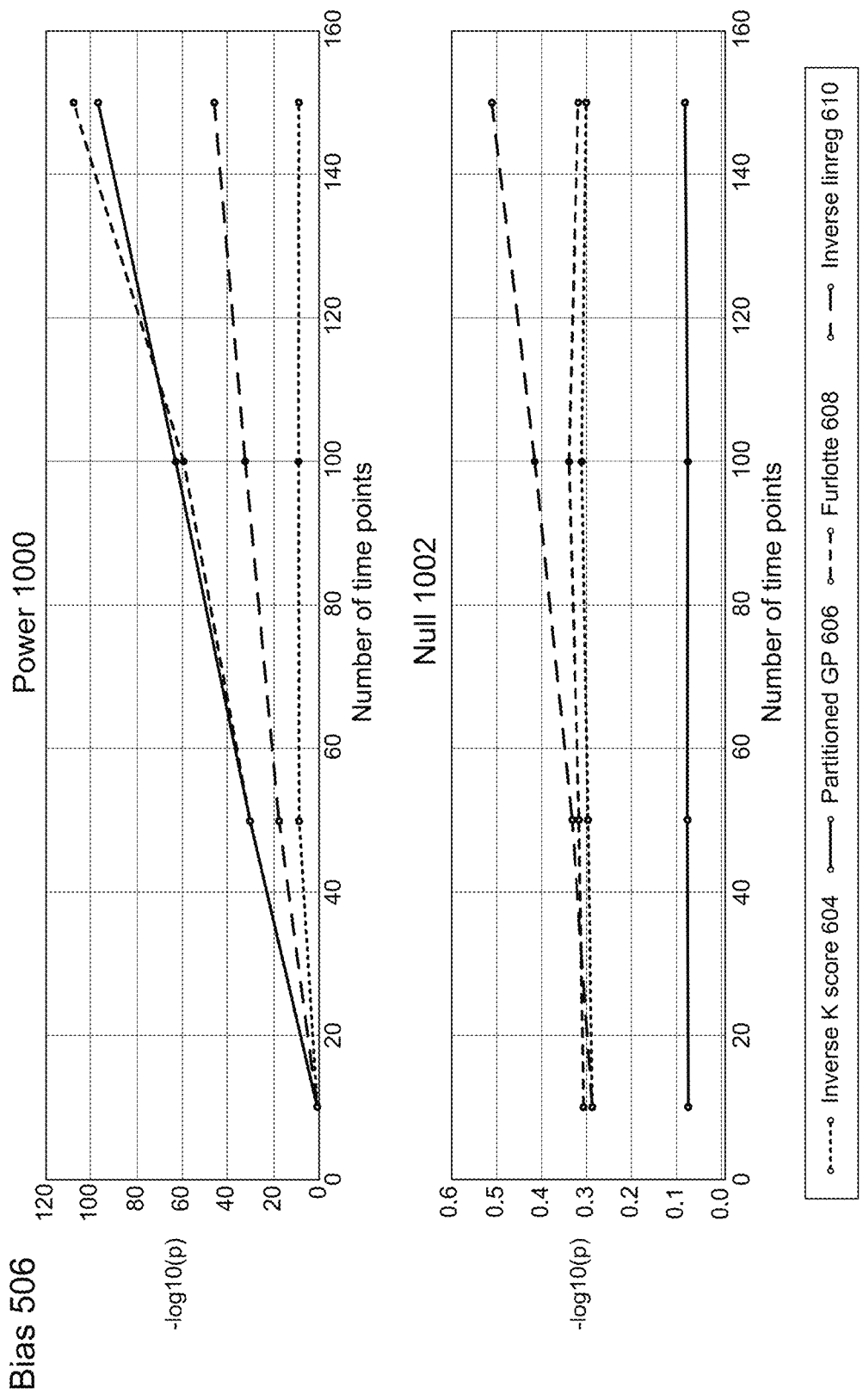
FIG. 10 shows the power curves of FIG. 6 limited to data exhibiting a bias trait.

FIGS. 7-10 show the data from FIG. 6 separated by trait type. FIG. 7 shows data for the wave 500 trait in a power plot 700 and a null plot 702 as described in FIG. 6. Similar to FIG. 6, when the data is limited to the wave 500 trait, Partitioned GP 606 has the greatest statistical power and inverse linreg 610 fails to control type I error. FIG. 8 shows data for the stretch 402 trait in a power plot 800 and a null plot 802 as described in FIG. 6. Partitioned GP 606 again has the most power, but Furlotte 608 despite only modelling a mean shift in the trait, is able to capture stretch with almost as much power. However, as shown in FIG. 7, Furlotte 608 has much lower power when analyzing the wave 500 trait, for which the mean between alleles is identical. FIG. 9 shows analysis of the linear 404 trait in which all models other than Inverse K score 604 work equally well as shown in the power plot 900. Inverse linreg 610 again suffers from failing to control type I error as shown in the null plot 902. FIG. 10 shows that when the trait is bias 406, in the power plot 1000 both Partitioned GP 606 and Furlotte 608 have equally good power. In the null plot 1002 Inverse linreg 610 is shown as failing to control type I error. Thus, Partitioned GP 606 has the best power over all as shown by FIG. 6 and when analyzing traits that behave as a wave 500 or stretch 402. Note also that Partitioned GP 606 has the lowest values in the null plots 602, 702, 802, 902, and 1002. The low values are not deficiencies as any value at or below the mid-point of the vertical axis of FIGS. 6-10 indicates control of type I error.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document. "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A computationally-efficient method for identifying a correlation between a single-nucleotide polymorphism (SNP) and a function-valued trait in a genome-wide association study (GWAS), the method comprising:

for a plurality of subjects, populating a trait matrix with values of the function-valued trait, a domain matrix with values of a plurality of function domain points, and a genotype matrix with allele values of the SNP;

linking the trait matrix, the domain matrix, and the genotype matrix;

generating a null model comprising a Gaussian distribution of the trait matrix with mean zero and a first covariance term, the first covariance term being determined in part by a first radial basis function (RBF) kernel applied to the domain matrix and in part by a first length-scale parameter;

representing the first covariance term as a first Kronecker product;

calculating a first maximum likelihood for the null model;

partitioning the matrix into a first partition, a second partition, and a third partition based at least in part on alleles of the SNP;

generating an alternative model that sums together Gaussian distributions of the first partition, the second partition, and the third partition of the matrix, each with mean value and a second, third, and fourth covariance term determined in part by a second, third, and fourth RBF kernel applied to first data from the domain matrix in the first partition, second data from the domain matrix in the second partition, and third data from the domain matrix in the third partition of the matrix and a second set of one or more length-scale parameters;

representing the second, third and fourth covariance terms as a second, third, and fourth Kronecker product;

calculating a second maximum likelihood for the alternative model;

calculating a difference between the first maximum likelihood for the null model and the second maximum likelihood for the alternative model;

calculating a test statistic based at least in part on the difference; and identifying existence of the correlation between the SNP and the function-valued trait based at least in part on the test statistic.

Clause 2. The method of clause 1, wherein the second set of one or more length-scale parameters comprises a single length-scale parameter shared across the first partition, the second partition, and the third partition.

Clause 3. The method of any one of clauses 1-2, wherein the second set of length-scale parameters comprises a first length-scale parameter associated with the first partition, a second length-scale parameter associated with the second partition, and a third length-scale parameter associated with the third partition.

Clause 4. The method of any one of clauses 1-3, wherein the first covariance term of the Gaussian distribution includes an NT×NT identity matrix, wherein N is a number of the plurality of subjects and T is a number of the plurality of function domain points.

Clause 5. The method of any one of clauses 1-4, wherein the first covariance term is defined in part by a first covariance matrix, the second covariance term is defined in part by a second covariance matrix, the third covariance term is defined in part by a third covariance matrix, and the fourth covariance term is defined in part by a fourth covariance matrix, all of which define similarites across subjects based in part on population structures, on family structures, or on other forms of similarity between subjects.

Clause 6. A computing device for identifying correlations in genome-wide association studies (GWAS), the computing device comprising:

a processing unit;
a memory;
a network connector;
input/output components;

a null model of data encoding absence of a correlation between a single-nucleotide polymorphism (SNP) and function-valued trait, the null model comprising a Gaussian distribution with a first covariance term determined in part by a non-linear kernel having a kernel-associated parameter;

an alternative model of the data encoding the correlation between the SNP and the function-valued trait, the alternative model comprising summation of separate Gaussian distributions each representing an effect of a single allele of the SNP or an effect of interaction between the SNP and at least one other SNP on the function-valued trait;

a model modification module, stored in the memory and implemented by the processing unit, configured to modify the null model and the alternative model by addition of pseudo-observations that make observations within the data conditionally independent; and a model comparison module, stored in the memory and implemented by the processing unit, configured to:
find, by way of an optimization procedure, a first likelihood of the data fitting the null model;
find, by way of the optimization procedure, a second likelihood of the data fitting the alternative model;
determine that the second likelihood of the data fitting the alternative model is higher than the first likelihood of the data fitting the null model; and
send an indication to at least one of the network connector or the input/output components that the function-valued trait is correlated with the SNP.

Clause 7. The computing device of clause 6, wherein the null model and the alternative model enforce smooth variation of the function-valued trait across a function domain.

Clause 8. The computing device of clause 7, wherein the kernel-associated parameter determines an overall scale on which the function-valued trait varies, where the scale is defined with respect to the function domain.

Clause 9. The computing device of any one of clauses 6-8, wherein the non-linear kernel comprises a radial basis function (RFB) kernel and the kernel-associated parameter comprises a length-scale parameter.

Clause 10. The computing device of any one of clauses 6-9, wherein the optimization procedure maximizes the lower bound of the null likelihood and the lower bound of the alternative likelihood, by way of variational inference.

Clause 11. The computing device of any one of clauses 6-10, wherein the model comparison module is further configured to:
specify a number of the pseudo-observations and not specify locations of the pseudo-observations; and
learn the position of pseudo-observations as part of the optimization procedure.

Clause 12. The computing device of any one of clauses 6-11, further comprising obtaining a value of the kernel-associated parameter by a quasi-Newton method of optimization.

Clause 13. The computing device of any one of clauses 6-12, wherein the pseudo-observations are shared across the multiple separate models in the alternative model.

Clause 14. The computing device of any one of clauses 6-13, wherein the data is provided to the Gaussian distribution as a vector derived from unrolling a matrix containing data for the traits of the subjects at function domain points.

Clause 15. A computationally-efficient method for identifying a correlation between a single-nucleotide polymorphism (SNP) and a function-valued trait in genome-wide association study (GWAS), the method comprising:

creating a linked matrix having values of the function-valued trait, values of function domain points, and phenotype values for each allele combination of the SNP;

generating an alternative model having a single Gaussian process of a vector derived from the linked matrix and a covariance term, the covariance term based upon at least one scalar and a non-linear kernel;

generating a null model by setting a value of the at least one scalar to zero;

comparing a first maximum likelihood for the alternative model with a second maximum likelihood for the null model; and determining that the SNP is correlated with the function-valued trait.

Clause 16. The method of clause 15, wherein the non-linear kernel is a radial basis function (RBF) kernel or a Matern kernel.

Clause 17. The method of any one of clauses 15-16, wherein the at least one scalar comprises a correlation parameter for each pair of alleles of the SNP indicating a degree of trait similarity between the data with each allele in the pair.

Clause 18. The method of any one of clauses 15-17, wherein the alternative model comprises a parameter that determines an overall scale on which the function-valued trait varies as a function varies.

Clause 19. The method of any one of clauses 15-18, further comprising:

determining that there are no missing data in the values of the function-valued trait and that the function domain points for each of the plurality of subjects align; and decomposing at least part of the covariance term to a Kronecker product thereby reducing computational time and memory needed to calculate the first maximum likelihood for the alternative model.

Clause 20. The method of any one of clauses 15-19, further comprising:

marginalizing over the missing values of the function-valued trait;

adding pseudo-observations as inputs to the non-linear kernel thereby making the values of the function-valued trait conditionally independent and reducing a time complexity for maximizing a lower bound of the first likelihood and a lower bound of the second likelihood, wherein variational inference maximizes a lower bound of the first likelihood and maximizes a lower bound of the second likelihood.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

Unless otherwise noted, all of the methods and processes described above may be embodied in whole or in part by software code modules executed by one or more general purpose computers or processors. The code modules may be stored in any type of computer-readable storage medium or other computer storage device. Some or all of the methods may alternatively be implemented in whole or in part by specialized computer hardware, such as FPGAs, ASICs, etc.

Conditional language such as, among others, "can," "could," "might" or "may," unless specifically stated otherwise, are used to indicate that certain embodiments include, while other embodiments do not include, the noted features, elements and/or steps. Thus, unless otherwise stated, such conditional language is not intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Conjunctive language such as the phrase "at least one of X, Y or Z," unless specifically stated otherwise, is to be understood to present that an item, term, etc. may be either X, or Y, or Z, or a combination thereof.

Many variations and modifications may be made to the above-described embodiments, the elements of which are to be understood as being among other acceptable examples. All such modifications and variations are intended to be included herein within the scope of this disclosure.

All publications referenced herein are incorporated by reference both for the specific teachings for which the individual publications are cited and for everything disclosed within the referenced publications.

The invention claimed is:

1. A computationally-efficient method for identifying a correlation between a single-nucleotide polymorphism (SNP) and a function-valued trait in a genome-wide association study (GWAS), the method comprising:

populating a matrix of values of the function-valued trait for a plurality of subjects at a plurality of function domain points;

generating a null model comprising a Gaussian distribution of the matrix with mean zero and a first covariance term, the first covariance term being determined in part by a first non-linear kernel applied to the plurality of function domain points for the function-valued trait and by a first parameter;

representing the first covariance term as a first Kronecker product;

calculating a first maximum likelihood for the null model;

partitioning the matrix into a first partition, a second partition, and a third partition based at least in part on alleles of the SNP;

generating an alternative model that sums together Gaussian distributions of the first partition, the second partition, and the third partition of the matrix with mean zero and a second covariance term determined in part by a second non-linear kernel applied to the first partition, the second partition, and the third partition of the matrix and a second parameter;

representing the second covariance term as a second Kronecker product;

calculating a second maximum likelihood for the alternative model;

calculating a difference between the first maximum likelihood for the null model and the second maximum likelihood for the alternative model;

calculating a test statistic based at least in part on the difference; and identifying existence of the correlation between the SNP and the function-valued trait based at least in part on the test statistic.

2. The method of claim 1, further comprising determining that a first Gaussian distribution of the first partition is different from a second Gaussian distribution of the second partition and from a third Gaussian distribution of the third partition.

3. The method of claim 1, further comprising determining that a first Gaussian distribution of the first partition has a different length scale and a different variance parameter than a second Gaussian distribution of the second partition and different than a third Gaussian distribution of the third partition.

4. The method of claim 1, wherein the non-linear kernel comprises a radial basis function (RBF) kernel.

5. The method of claim 1, wherein the first parameter comprises a first length-scale parameter that determines a first scale on which the function-valued trait varies within individual ones of the plurality of subjects and the second parameter comprises a second length-scale parameter that determines a second scale on which the function-valued trait varies within individual ones of the plurality of subjects.

6. A computationally-efficient method for identifying a correlation between a single-nucleotide polymorphism (SNP) and a function-valued trait in genome-wide association study (GWAS), the method comprising:
creating a linked matrix having values of the function-valued trait, values of function domain points, and phenotype values for each allele combination of the SNP;
generating an alternative model having a single Gaussian process of a vector derived from the linked matrix and a covariance term, the covariance term based upon at least one scalar and a non-linear kernel;
generating a null model by setting a value of the at least one scalar to zero;
comparing a first maximum likelihood for the alternative model with a second maximum likelihood for the null model; and
determining that the SNP is correlated with the function-valued trait based on the comparison of the first maximum likelihood for the alternative model with the second likelihood for the null model.

7. The method of claim 6, wherein the non-linear kernel is a radial basis function (RBF) kernel or a Matern kernel.

8. The method of claim 6, wherein the at least one scalar comprises a correlation parameter for each pair of alleles of the SNP indicating a degree of trait similarity between the data with each allele in the pair.

9. The method of claim 6, wherein the alternative model comprises a parameter that determines an overall scale on which the function-valued trait varies as a function varies.

10. The method of claim 6, further comprising:
determining that there are no missing data in the values of the function-valued trait and that the function domain points for each of the plurality of subjects align; and
decomposing at least part of the covariance term to a Kronecker product thereby reducing computational time and memory needed to calculate the first maximum likelihood for the alternative model.

11. The method of claim 6, further comprising:
marginalizing over the missing values of the function-valued trait; and
adding pseudo-observations as inputs to the non-linear kernel thereby making the values of the function-valued trait conditionally independent and reducing a time complexity for maximizing a lower bound of the first likelihood and a lower bound of the second likelihood, wherein variational inference maximizes a lower bound of the first likelihood and maximizes a lower bound of the second likelihood.

12. A computationally-efficient system for identifying a correlation between a single-nucleotide polymorphism (SNP) and a function-valued trait in genome-wide association study (GWAS), the system including:
a data storage device that stores instructions for identifying a correlation between a single-nucleotide polymorphism (SNP) and a function-valued trait in genome-wide association study (GWAS); and
a processor configured to execute the instructions to perform a method including:
creating a linked matrix having values of the function-valued trait, values of function domain points, and phenotype values for each allele combination of the SNP;
generating an alternative model having a single Gaussian process of a vector derived from the linked matrix and a covariance term, the covariance term based upon at least one scalar and a non-linear kernel;
generating a null model by setting a value of the at least one scalar to zero;
comparing a first maximum likelihood for the alternative model with a second maximum likelihood for the null model; and
determining that the SNP is correlated with the function-valued trait based on the comparison of the first maximum likelihood for the alternative model with the second likelihood for the null model.

13. The system of claim 12, wherein the non-linear kernel is a radial basis function (RBF) kernel or a Matern kernel.

14. The system of claim 13, wherein the at least one scalar comprises a correlation parameter for each pair of alleles of the SNP indicating a degree of trait similarity between the data with each allele in the pair.

15. The system of claim 13, wherein the alternative model comprises a parameter that determines an overall scale on which the function-valued trait varies as a function varies.

16. The system of claim 12, wherein the at least one scalar comprises a correlation parameter for each pair of alleles of the SNP indicating a degree of trait similarity between the data with each allele in the pair.

17. The system of claim 16, wherein the non-linear kernel is a radial basis function (RBF) kernel or a Matern kernel.

18. The system of claim 12, wherein the alternative model comprises a parameter that determines an overall scale on which the function-valued trait varies as a function varies.

19. The system of claim 12, wherein the processor is further configured to execute the instructions to perform the method further including:
determining that there are no missing data in the values of the function-valued trait and that the function domain points for each of the plurality of subjects align; and
decomposing at least part of the covariance term to a Kronecker product thereby reducing computational time and memory needed to calculate the first maximum likelihood for the alternative model.

20. The system of claim 12, wherein the processor is further configured to execute the instructions to perform the method further including
marginalizing over the missing values of the function-valued trait; and
adding pseudo-observations as inputs to the non-linear kernel thereby making the values of the function-valued trait conditionally independent and reducing a time complexity for maximizing a lower bound of the first likelihood and a lower bound of the second likelihood, wherein variational inference maximizes a lower bound of the first likelihood and maximizes a lower bound of the second likelihood.

* * * * *